US012564598B2

(12) United States Patent
Kim et al.

(10) Patent No.: US 12,564,598 B2
(45) Date of Patent: Mar. 3, 2026

(54) NITRIC OXIDE-SENSITIVE HYDROGEL

(71) Applicant: POSTECH RESEARCH AND BUSINESS DEVELOPMENT FOUNDATION, Pohang-si (KR)

(72) Inventors: Won Jong Kim, Pohang-si (KR); Tae Jeong Kim, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 311 days.

(21) Appl. No.: 18/277,652

(22) PCT Filed: Jan. 10, 2022

(86) PCT No.: PCT/KR2022/000357

§ 371 (c)(1),
(2) Date: Aug. 17, 2023

(87) PCT Pub. No.: WO2022/177151

PCT Pub. Date: Aug. 25, 2022

(65) Prior Publication Data

US 2024/0165128 A1 May 23, 2024

(30) Foreign Application Priority Data

Feb. 18, 2021 (KR) ........................ 10-2021-0021980

(51) Int. Cl.

| | |
|---|---|
| ***A61K 31/573*** | (2006.01) |
| ***A61K 9/00*** | (2006.01) |
| ***A61K 9/06*** | (2006.01) |
| ***A61K 45/06*** | (2006.01) |
| ***A61P 19/02*** | (2006.01) |

(52) U.S. Cl.

CPC .......... *A61K 31/573* (2013.01); *A61K 9/0019* (2013.01); *A61K 9/06* (2013.01); *A61K 45/06* (2013.01); *A61P 19/02* (2018.01)

(58) Field of Classification Search

None

See application file for complete search history.

(56) References Cited

U.S. PATENT DOCUMENTS

| | | | |
|---|---|---|---|
| 2018/0339063 | A1 | 11/2018 | Ulman et al. |
| 2020/0040145 | A1 | 2/2020 | Kim et al. |
| 2020/0085809 | A1 | 3/2020 | Bright et al. |

FOREIGN PATENT DOCUMENTS

| | | |
|---|---|---|
| KR | 10-2020-0025379 | 3/2020 |
| WO | 2013-127949 | 9/2013 |
| WO | 2017083659 | 5/2017 |

OTHER PUBLICATIONS

Park et al., Advanced Materials (2017), 29(44), 1702859, 8 pages.*

EPO, Search Report of EP 22756357.4 dated Nov. 27, 2024, total 18 pages.

Quang Vinh Nguyen et al., "Injectable polymeric hydrogels for the delivery of therapeutic agents: A review", European Polymer Journal, vol. 72, Mar. 14, 2015, pp. 602-619.

Zihao Xu et al., "Click Chemistry and Material Selection for in Situ Fabrication of Hydrogels in Tissue Engineering Application", ACS Biomater. Sci. Eng. 2018, vol. 4, May 26, 2018, pp. 2276-2291.

Janarthanan Gopinathan et al., "Click Chemistry-Based Injectable Hydrogels and Bioprinting Inks for Tissue Engineering Applications", Tissue Eng Regen Med., vol. 15, No. 5, Aug. 16, 2018, pp. 531-546.

Akira Takahashi et al., "in situ cross-linkable hydrogel of hyaluronan produced via copper-free click chemistry", Biomacromolecules, vol. 14, No. 10, Oct. 14, 2013, pp. 3581-3588.

Jiwon Yeo et al., "Nitric Oxide-Scavenging Nanogel for Treating Rheumatoid Arthritis", Nano letters, 19(10), 6716-6724, May 17, 2019, total 25 pages.

Junghong Park et al., "Therapeutic-Gas-Responsive Hydrogel", Advanced Materials, 29(44), 1702859, Oct. 11, 2017, total 8 pages.

Angela Scala et al., ""Click" on PLGA-PEG and hyaluronic acid: Gaining access to anti-leishmanial pentamidine bioconjugates", Joumal of Biomedical Materials Research Part B: Applied Biomaterials, 106(8), 2778-2785., Dec. 8, 2017, total 8 pages.

* cited by examiner

*Primary Examiner* — Brian J Davis

(74) *Attorney, Agent, or Firm* — LEX IP MEISTER, PLLC

(57) ABSTRACT

The present disclosure relates to a nitric oxide-sensitive hydrogel. The hydrogel is formed through in-situ hybridization in a target site by means of a click chemical reaction and is prepared using a nitric oxide-sensitive crosslinker. The hydrogel can effectively collect and scavenge nitric oxide overexpressed in the target site, and a drug loaded in the hydrogel can be locally and sensitively released to a target site to be treated. Therefore, the hydrogel can be effectively used to prevent and treat inflammatory disease caused by the overexpression of nitric oxide.

9 Claims, 21 Drawing Sheets

4-nitro-O-phenylenediamine 1 2

3 4 (DA-NOCCL)

PEG monoTos-PEG monoBr-PEG

PLA-*b*-PEG-Br

PLA-*b*-PEG-$N_3$

TNF-α (pg/mL)
1000
800
600
400
200
0
***

***
**
***
LPS (−) (+) (+) (+)
Sample (−) (−) M-NO Ctrl IL-6 (pg/mL)
600
400
200
0
***

***
**
***
LPS (−) (+) (+) (+)
Sample (−) (−) M-NO Ctrl M-NO gel
Ctrl gel
RAW 264.7
NIH/3T3
LPS (+) (−) (+) (−)

Relative swelling ratio
6
4
2
0
**
n.s.
M-NO gel
Ctrl gel
LPS (+) (−) (+) (−)
LPS
RAW 264.7
NO release IL-6
TNF-α
NO scavenging/ Gel swelling Clincal score (a.u.)
Time (week)

Latency to fall (s)
n.s.
(A) (B) (C) (D) (E) (F) (G) (H)

NITRIC OXIDE-SENSITIVE HYDROGEL

TECHNICAL FIELD

The present disclosure relates to a nitric oxide-sensitive hydrogel. The hydrogel is formed through in-situ hybridization in a target site by means of a click chemical reaction and is prepared using a nitric oxide-sensitive crosslinker, and thus can effectively collect and scavenge nitric oxide overexpressed in the target site, and a drug loaded in the hydrogel can be locally and sensitively released to a target site to be treated so as to be effectively usable in preventing or treating inflammatory disease caused by the overexpression of nitric oxide.

BACKGROUND ART

Nitric oxide is a highly reactive radical molecule with a short half-life of a few seconds. Nitric oxide is produced by various cells in the human body and is known to play a variety of roles in the body, including neurotransmission, vasodilation, and anticancer activities, depending on its concentration.

Since the late 2010s attempts to locally and selectively capture overproduced nitric oxide at the site of a disease have been actively pursued to alleviate or treat inflammatory diseases caused by the overproduction of nitric oxide.

In response to these attempts, nanometer-scale technologies have been developed for ease of injection, but they suffer from rapid diffusion and removement to organs other than the injection site. For example, nitric oxide plays an important role in the body in normal ranges, so non-specific removal of nitric oxide can lead to numerous side effects, such as systemic toxicity. In rheumatoid arthritis, a chronic inflammatory disease, intra-cartilage injections are given up to three to four times a year, so a technology that can rapidly diffuse or remove nitric oxide to organs other than the site of the disease is undesirable.

On the other hand, Rheumatoid arthritis is a chronic inflammatory disease of unknown cause characterized by multiple arthritis. In the beginning, inflammation occurs in the synovial membrane covering the joint, but gradually the inflammation spreads to the surrounding cartilage and bone, resulting in the destruction and deformation of the joint. It is a disease that can invade the whole body and includes diseases such as anemia, xerostomia, subcutaneous nodular pulmonary fibrosis, vasculitis, and skin ulcers with not only joint but also extra-articular symptoms.

Although the exact cause of rheumatoid arthritis has not yet been identified, autoimmunity is known to be the main mechanism. Autoimmunity is a phenomenon in which the immune system, which protects the body from the outside, attacks its own body rather than the abnormality. Genetic predisposition, bacterial or viral infections, and other factors are generally thought to cause rheumatoid arthritis.

Rheumatoid arthritis is an intractable autoimmune disease accompanied by joint swelling, inflammation, stiffness, and pain, and shows symptoms of polyarthritis throughout the body, causing a lot of pain to patients with the disease.

Therefore, there is a need for new technologies that can locally capture nitric oxide at the target site for a prolonged period of time, and furthermore, deliver therapeutic agents in response to nitric oxide to alleviate or treat diseases associated with nitric oxide overexpression.

DISCLOSURE

Technical Problem

Provided is a nitric oxide-sensitive hydrogel that can locally capture and eliminate nitric oxide overproduced in the body and further provides a nitric oxide-sensitive hydrogel that can be used for the prevention or treatment of inflammatory diseases by locally and selectively releasing a drug carried in the hydrogel to a disease site depending on the concentration of nitric oxide.

Technical Solution

These will be described in detail below. All combinations of the various elements disclosed in the present disclosure fall within the scope of the present disclosure. Furthermore, the scope of the present disclosure shall not be deemed to be limited by the following specific description.

The present disclosure provides an in-situ hybridization hydrogel prepared from compounds represented by Formulae 1 to 3 below.

[Formula 1]

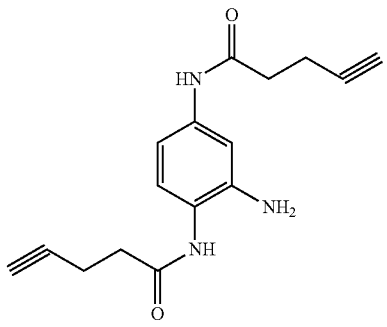

[Formula 2]

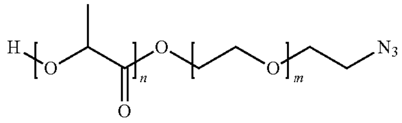

[Formula 3]

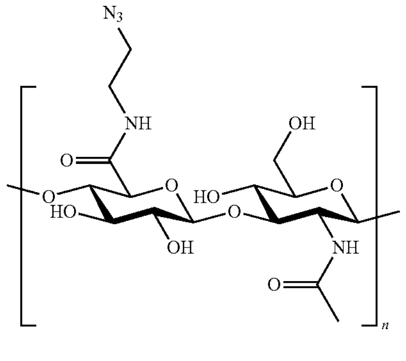

Where, the $R_1$ and $R_2$ are each independently C1 to C10 alkylene, and the n and m are each an integer of 1 to 1000.

As used herein, "Cx-Cy" (where x and y are integers greater than or equal to 1) refers to a carbon number. For example, C1 to C10 alkylene means an alkylene having a carbon number of at least 1 and no more than 10, and C1 to C10 alkyl means an alkyl having a carbon number of at least 1 and no more than 10.

As used herein, "alkyl" means a straight-chain or branched-chain saturated hydrocarbon group, including methyl, ethyl, n-propyl, isopropyl, n-butyl, sec-butyl, isobutyl, tert-butyl, n-pentyl, n-hexyl, n-heptyl, n-octyl, n-nonyl, n-decanyl, and the like.

As used herein, "alkylene" means a divalent functional group derived from an alkyl as defined above.

In the present disclosure, "in-situ" may be used interchangeably with "in place" or "in-situ" and means "at the site of administration" or "at the target site".

In the present disclosure, "in-situ hybridization" means that precursor materials capable of forming a hydrogel are injected into a patient's body, and then gelation occurs by binding of the precursor materials at a targeted site in a tissue, organ, or body cavity of the desired body.

In the present disclosure, "patient" refers to any individual or entity in need of treatment for a particular condition or disease and may be a mammal, preferably a human.

The in-situ hybridization hydrogel of the present disclosure does not require a surgical procedure for implantation, and the hydrogel is formed in the body through a minimally invasive technique by simply mixing precursor materials, which can provide comfort to the patient receiving the treatment, and the hydrogel can be formed locally and selectively in the target site of the body, which has a particularly good therapeutic effect on the site in need of treatment.

In the present disclosure, the compound represented by Formula 1 may act as a crosslinking agent in the formation of a hydrogel.

[Formula 1]

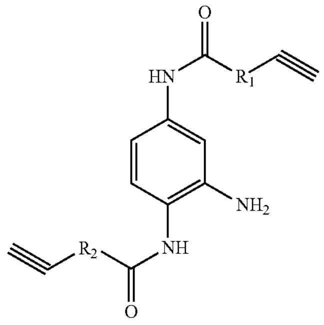

(The $R_1$ and $R_2$ are each independently C1 to C10 alkylene)

In this disclosure, the term "crosslinking agent" refers to a material for binding compounds to each other to take a network structure, and in accordance with embodiments of this disclosure, the compound represented by Formula 1 may be, but is not limited to, the compound represented by the formula DA-NOCCL, in which $R_1$ and $R_2$ are C2 alkylenes

[DA-NOCCL]

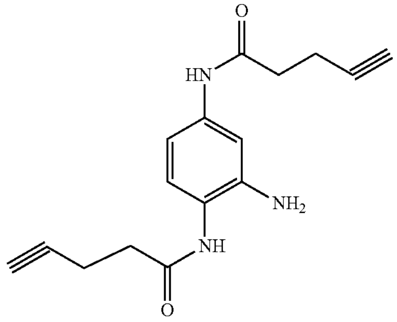

Since the compounds represented by Formula 1 may act to capture and eliminate overproduced nitric oxide, a hydrogel of the present disclosure prepared using the compounds represented by Formula 1 may capture and eliminate overproduced nitric oxide in the body.

Further, the compounds of the disclosure represented by Formula 1 may be degradable in response to nitric oxide, and the hydrogels of the disclosure prepared from the compounds represented by Formula 1 may be degradable in response to nitric oxide.

In the present disclosure, "sensitive" means sensitive to any environmental condition, and the terms "sensitive" and "responsive" may be used interchangeably herein.

The following experimental examples demonstrate that the hydrogel of the present disclosure can absorb nitric oxide and expand, thereby collecting and scavenging nitric oxide overproduction in the body and effectively treating diseases caused by nitric oxide overproduction. Furthermore, it has been demonstrated that the hydrogel of the present disclosure can be degraded in response to nitric oxide, thereby enabling the selective release of the micelle structures bound within the hydrogel reticular structure to the diseased site and the localized, selective, and concentrated delivery of the drug carried in the micelle structures to the diseased site. In addition, it was confirmed that the hydrogel of the present disclosure could be degraded in a NO concentration-dependent manner, thus enabling adjustment of drug release according to the severity of the disease.

In the present disclosure, the compound represented by Formula 2, also referred to as PLA-b-PEG-N3 block copolymer, can be bound to the alkyne group of the compound represented by Formula 1 by a click chemistry reaction via an azide group.

[Formula 2]

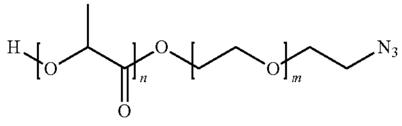

(Where n and m are each an integer of 1 to 1000)

The compound represented by Formula 2 may form a micelle structure by self-assembly.

In the present disclosure, "micelle" refers to a system composed of an inner hydrophobic region and an outer hydrophilic region in an aqueous solution, and in the present disclosure, a PLA-b-PEG-N3 block copolymer, a compound represented by the formula 2, was used to form a micelle structure.

In the present disclosure, the micelle structure carries a hydrophobic drug and is released specifically to the disease site, enabling a combined treatment, i.e., treatment by nitric oxide scavenging and treatment by the drug, in treating diseases caused by overproduced nitric oxide.

According to embodiments of the present disclosure, the micelle structures may have a uniform diameter of 10 to 1000 nm, preferably 70 to 900 nm, and even more preferably 70 to 500 nm. When the diameter is less than the above range, the micelle structure may not be possible to carry enough drugs to treat the disease to be treated, and when the diameter exceeds the above range, they may not be suitable in terms of ease of injection.

In the present disclosure, the micelle structure may be fixed to the network structure of the hydrogel. The micelle structure can be released from the hydrogel when the hydrogel is degraded in response to nitric oxide and can selectively deliver the carried drug to the site where nitric oxide is overproduced.

In the present disclosure, the hyaluronic acid-based polymer chain, which is a compound represented by Formula 3, is also referred to as HA-N3 and serves to form the hydrogel backbone of the present disclosure.

[Formula 3]

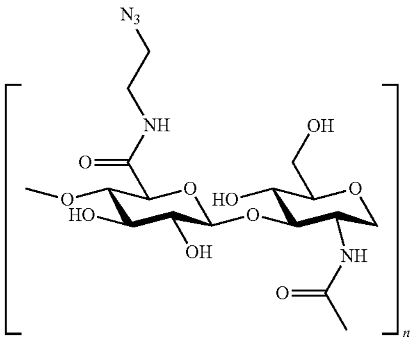

(Where n is an integer of 1 to 1000)

In the present disclosure, the "hyaluronic acid" is a linear polysaccharide composed of glucuronic acid and acetylglucosamine, one of the glycosaminoglycans present in the extracellular matrix (ECM), the synovial fluid of joints, and supports constituting cartilage. Cross-linked hyaluronic acid can be used as a synovial fluid of joints due to its viscoelastic properties, and cross-linked hyaluronic acid is a material with excellent biocompatibility that can be used for tissue engineering and drug delivery systems because there is no problem in terms of immunity when applied in vivo.

In the present disclosure, the compound represented by Formula 3 can be bound via an azide group to an alkyne group of the compound represented by Formula 1 by a click chemistry reaction.

In the present disclosure, the hydrogel may be prepared by a click chemistry reaction between the compound represented by Formula 1 and the compounds represented by Formulae 2 and 3 above.

In the present disclosure, "click chemistry" is a customized reaction that occurs in the complex environment of living organisms and means a modular approach to organic synthesis that combines rapidly, effectively, and predictably under specific conditions. For example, the azide-alkyne cyclo addition reaction can form bonds between azide and alkyne compounds in an efficient and high yield due to its very high thermodynamic driving force, which can also be used to form intermolecular bonds in high yield in reactions with polymers such as oligomers, polymers, etc.

According to embodiments of the present disclosure, an alkyne group of a compound represented by Formula 1 and an azide, —$N_3$, group of a compound represented by Formula 2; and the alkyne group of the compound represented by Formula 1 and the azide, —$N_3$ group of the compound represented by Formula 3, respectively, form a 1,2,3-triazole by click chemistry, which can form a nitric oxide reactive in-situ hybridization hydrogel including the micelle structure of the present disclosure.

In the present disclosure, the hydrogels may further enhance their effectiveness in treating inflammation or disease caused by overexpressed nitric oxide by including bioactive substances. In the present disclosure, the hydrogels may further enhance their effectiveness in treating inflammation or disease caused by overexpressed nitric oxide by including bioactive substances. Such bioactive substances may be substances used in the treatment, healing, prevention, or diagnosis of disease, such as, but not limited to, cells, proteins, or peptides such as growth factors and hormones, nucleic acids, extracellular matrix substances, and drugs with therapeutic properties, and any bioactive substance known to be effective against a particular disease may be incorporated into the hydrogel to enhance the therapeutic effect. To prepare a hydrogel to contain a bioactive substance, a solution can be prepared to contain the bioactive substance in one solution and can be mixed with the other solution at a target site to form a hydrogel. Additionally, each of the two solutions containing the bioactive substance can be mixed at the target site using a syringe to form a hydrogel.

In the present disclosure, the hydrogel may further include a hydrophobic drug, the hydrophobic drug being carried in a micelle structure formed by self-assembly of the compound represented by Formula 2. Since the micelle structure is formed by self-assembly of a block copolymer having hydrophilic and hydrophobic portions in water, the interior of the micelle structure is strongly hydrophobic, and thus the interior of the micelle structure is susceptible to being loaded with a hydrophobic drug, a physical phenomenon attributable to the hydrophobicity of both the drug and the interior of the micelle structure, which can increase the drug content relative to the drug delivery system due to chemical bonding.

In the present disclosure, "hydrophobic" means a non-polar or low-polar substance that is immiscible with water but is not limited thereto, and any substance that can stably exist inside the hydrophobic surface of the micelle structure of the present disclosure is a hydrophobic substance.

In the present disclosure, the hydrophobic drug may be selected from analgesics, anti-inflammatory agents, immunosuppressive agents, or combinations thereof, and may preferably be anti-inflammatory agents but is not limited thereto.

In the present disclosure, "anti-inflammatory agent" is also referred to as an anti-inflammatory agent and means a drug that has the property of scavenging inflammation or inhibits it by participating in the inflammatory process.

The anti-inflammatory agents may be at least one selected from the group consisting of, for example, 21-acetoxypregnenolone, alclomethasone, alclomethasone dipropionate, algestone, amcinonide, beclomethasone, betamethasone, betamethasone dipropionate, betamethasone sodium phosphate, betamethasone valerate, budesonide, chloroprednisone, ciclesonide, clobetasol, clobetasol-17-propionate, clobetasone-17-butyrate, clobetasone, chlorcortolone, clofrednol, corticosterone, cortisone, cortisone acetate, cortibazole, deflazacort, desonide, desoxymethasone, dexamethasone, dexamethasone sodium phosphate, diflorasone, diflucortolone, difluprednate, enoxolone, fluazacort, flucloronide, flumethasone, fluocinonide, fluocinolone, fluocinolone acetonide, fluocinonide, fluocortin butyl, fluocortolone, fluocortolone caproate, fluocortolone pivalate, fluorometholone, flunisolid, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, hydrocortisone acetate, hydrocortisone-17-acetonate, hydrocortisone-17-buteprate, hydrocortisone-17-butyrate, hydrocortisone-17-valerate, loteprednol, mazipredone, medrysone, meprednisone, methylprednisolone, mometasone, mometasone furoate, parametasone, parametasone acetate, prednicarbate, prednisolone, prednisolone 25-diethylamino-acetate, prednisolone sodium phosphate, prednisone, prednival, prednylidene, remexolone, tixocortol, tixocortol pivalate, triamcinolone, triamcinolone acetonide, triamcinolone alcohol, triamcinolone benetonide, and triamcinolone hexacetonide, and according to embodiments of the present disclosure, the anti-inflammatory agent may be dexamethasone, but is not limited thereto.

Furthermore, according to embodiments of the present disclosure, the hydrophobic drug may be included at 3% to 7% by weight of the total weight of the micelle structure but is not limited thereto.

The hydrogel of the present disclosure may further include a hydrophobic drug and a hydrophilic drug.

In the present disclosure, the hydrophobic drug and the hydrophilic drug may be released simultaneously from the target site, in which the release of the hydrophobic drug is due to erosion-based release and the release of the hydrophilic drug is due to Fickian diffusion.

The experimental examples described below confirm that the hydrogel of the present disclosure can include a hydrophobic drug in the micelle, which is the hydrophobic domain of the hydrogel, and a hydrophilic drug in the hydrophilic domain of the hydrogel, and that the two drugs can be released simultaneously at the target site requiring treatment. In addition, the degree of drug release from the hydrogel of the present disclosure can vary depending on the concentration of nitric oxide, which means that drug release can be adjusted according to the severity of the disease, indicating that customized treatment is possible according to the condition of the disease to be treated.

The compounds of Formulae 1 to 3 for preparing the hydrogels in the present disclosure may be co-injected into the target site.

In the present disclosure, "co-injection" means that the compounds of Formulae 1 to 3 are injected together in a formulation suitable for injection, e.g., in a liquid state, into a targeted site in a patient's body. According to embodiments of the present disclosure, a composition in liquid form including a compound of Formulae 1 to 3 is homogeneously mixed before entering a target site in a patient's body after exiting from the tip of an injection needle and is then injected into the target site as a mixture, and is gelled in the body. The compounds of Formulae 1 to 3 of the present disclosure can be co-injected into the target site and then spontaneously combined by a click chemistry reaction to form a hydrogel.

In the present disclosure, the simultaneous injection may be achieved using a dual syringe system or any other suitable syringe system, preferably by a dual syringe system. According to embodiments of the present disclosure, the compounds represented by Formulae 1 to 3 may be physically separated before simultaneous injection, for example, simultaneous extrusion by injection, mixing, and a series of injections through needles occur in the patient's body. According to embodiments of the disclosure, the composition including the compounds represented by Formula 1 and Formula 3 can be physically separated from the composition including the compound represented by Formula 2. According to embodiments of the disclosure, the compositions including the compounds represented by Formula 1 and Formula 2 may be physically separated from the compounds represented by Formula 3. According to embodiments of the present disclosure, a composition including a compound represented by Formula 1 may be physically separated from compounds represented by Formula 2 and Formula 3.

The hydrogel of the present disclosure may be formed within 0.5 to 10 minutes, preferably within 0.5 to 1 minute, after injection of a compound of Formulae 1 to 3 into a target site. When the hydrogel formation time (gelation time) is less than the above range, injection into the target site may not be smooth due to premature cross-linking after mixing of the compounds represented by Formulae 1 to 3, and when the hydrogel formation time exceeds the above range, the injected substances may diffuse into the surrounding tissue and may not be suitable for the formation of a localized hydrogel at the target site. Conventional in-situ injectable hydrogels developed through temperature or UV irradiation have problems such as slow phase transition time. The hydrogel of the present disclosure can gel in a short time through a click chemistry reaction, solving the problems of the related previous art.

The hydrogel of the present disclosure can be used for preventing, alleviating, or treating inflammatory diseases.

In the present disclosure, "inflammatory disease" means a disease in which inflammation is the main lesion, and in the present disclosure, the inflammatory disease may be an inflammatory disease indicating an overproduction of nitric oxide in a living body.

The hydrogel of the present disclosure can capture and eliminate overproduced nitric oxide. When the immune system collapses due to stress or the like, and nitric oxide is overproduced in vivo, an autoimmune disease or an inflammatory disease may be caused. Therefore, the hydrogel of the present disclosure capable of collecting and scavenging overproduced nitric oxide can effectively treat diseases caused by overproduction of nitric oxide.

Further, the inflammatory disease may be a disease caused by inflammation of a joint, such as undifferentiated spondyloarthropathy, undifferentiated arthropathy, arthritis, chronic inflammatory disease caused by a viral or bacterial infection, rheumatoid arthritis, reactive arthritis, osteoarthritis, osteoporosis, and the like, but is not limited thereto. According to embodiments of the present disclosure, the inflammatory disease may be rheumatoid arthritis but is not limited thereto.

The rheumatoid arthritis is one of the autoimmune diseases and is a disease caused by high concentrations of nitric oxide. Thus, the hydrogel of the present disclosure can capture nitric oxide in a high concentration of nitric oxide environment, inhibit cytokine-induced osteoclast bone resorption, and prevent cell death in the joint to alleviate or treat rheumatoid arthritis.

In the present disclosure, "alleviate or treatment" means to reduce the severity of disease symptoms, increase the frequency and duration of periods without disease symptoms, or prevent damage or disability caused by the suffering of disease.

The hydrogel of the present disclosure may reduce the levels of pro-inflammatory cytokines TNF-α and IL-6.

In the present disclosure, "pro-inflammatory cytokine" means a cytokine that is produced primarily by activated macrophages and promotes systemic inflammation. Pro-inflammatory cytokines include, for example, tumor necrosis factor-α (TNF-α), IL-1, IL-2, IL-6, and IL-8, which co-occur during an inflammatory response and can be indicators of an inflammatory response.

When the hydrogel of the present disclosure is treated in the experimental examples described later, it is confirmed that the levels of TNF-α and IL-6, which are pro-inflammatory cytokines, can be reduced, confirming that the hydrogel of the present disclosure can be useful for the treatment of inflammatory diseases.

The hydrogel of the present disclosure can be used for visco-supplement.

In the present disclosure, "visco-supplement" refers to a substance that replenishes mucous synovial fluid by injecting hyaluronic acid in a gel state into a joint.

In the experimental examples described below, the hydrogels of the present disclosure showed almost complete recovery from stress-induced flow after rupture, confirming their usefulness as biscuity supplements. This is believed to be due to intermolecular hydrogen bonding between HA chains and entropy-driven reassociation of the micelle structure, without being bound to a specific theory.

According to another aspect of the present disclosure, an in-situ hydrogel precursor composition including compounds represented by Formulae 1 to 3 is provided.

[Formula 1]

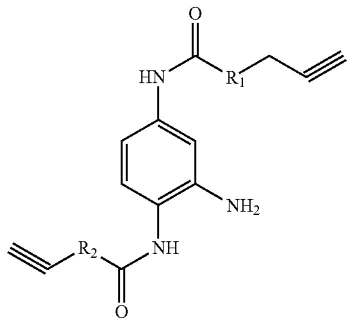

[Formula 2]

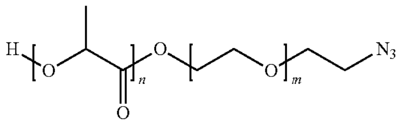

[Formula 3]

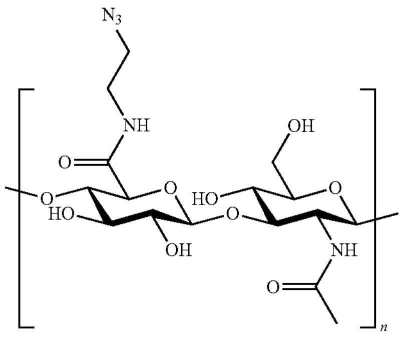

Where, the $R_1$ and $R_2$ are each independently C1 to C10 alkylene, and the n and m are each an integer of 1 to 1000.

In the present disclosure, "precursor" refers to a compound that participates in a chemical reaction that produces another compound.

The precursor composition of the present disclosure may further include a hydrophobic drug, and the hydrophobic drug may be carried on a micelle structure formed by self-assembly of the compound represented by Formula 2.

The precursor composition of the present disclosure may further include a hydrophobic drug and a hydrophilic drug.

According to another aspect of the present disclosure, a method for producing an in-situ hybridization hydrogel including the following steps is provided.

a) preparing a first precursor composition including a compound represented by Formula 1 and a compound represented by Formula 3;

b) preparing a second precursor composition including a micelle structure formed from a compound represented by Formula 2 below; and c) co-injecting the first precursor composition and the second precursor composition.

[Formula 1]

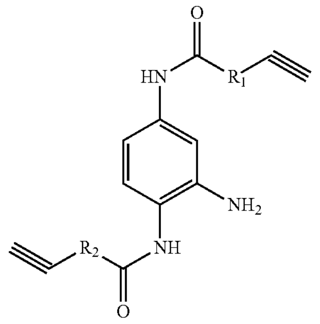

[Formula 2]

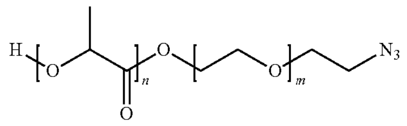

[Formula 3]

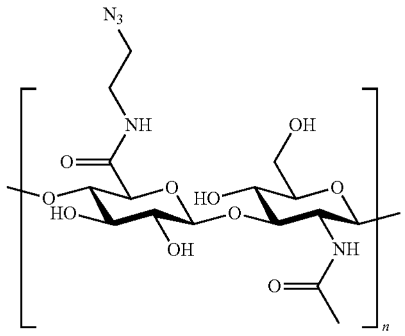

Where, the $R_1$ and $R_2$ are each independently C1 to C10 alkylene, and the n and m are each an integer of 1 to 1000.

According to embodiments of the disclosure, the compound represented by Formula 1 may be included in an amount of 0.02% to 0.06% by weight of the total mass of the first precursor composition; the compound represented by Formula 2 maybe included in an amount of 1.00% to 3.00% by weight of the total mass of the second precursor composition; and the compound represented by Formula 3 may be included in an amount of 1.00% to 1.50% by weight of the total mass of the first precursor composition, but is not limited thereto.

In the preparing methods of the present disclosure, the second precursor composition may further include a catalyst, and according to embodiments of the present disclosure, the catalyst may be Cu(I) but is not limited thereto.

In the preparing methods of the present disclosure, the second precursor composition may further include a hydrophobic drug, in which the hydrophobic drug is carried in a micelle structure formed by self-assembly of the compound represented by Formula 2.

In the preparing methods of the present disclosure, the first and second precursor compositions may further include a hydrophobic drug and a hydrophilic drug. According to embodiments of the disclosure, a hydrophobic drug may be included in the second precursor composition, a hydrophilic drug may be included in the first precursor composition, and both a hydrophobic drug and a hydrophilic drug may be included in the first precursor composition, or the second precursor composition, but is not limited thereto.

In the preparing method of the present disclosure, the co-injection may be performed by a dual syringe system.

In the preparing methods of the present disclosure, the first and second precursor compositions may be in the form of a suspension, solution, or emulsion suitable for parenteral administration, may be formulated in the form of a solid or semi-solid, and may include a formulating agent such as a suspending agent, stabilizing agent, dissolving agent, and/or dispersing agent.

According to embodiments of the present disclosure, the first and second precursor compositions may be in a liquid state or sterilized but are not limited thereto. The first and second precursors can be preserved against the contaminating action of microorganisms such as bacteria or fungi. Furthermore, the first and second precursor compositions may be in powder form and may be sterilized. In this case, they may be formulated in liquid form, for example, with water for injection before use.

The present disclosure provides a method of preventing, alleviating, or treating an inflammatory disease, including the step of administering a hydrogel of the present disclosure to an individual having the inflammatory disease.

In the present disclosure, "administration" means introducing the hydrogel of the disclosure into a patient by any suitable means, and the route of administration of the hydrogel of the disclosure may be by any conventional route as long as it can reach the tissue of interest but is preferably parenteral. The parenteral administration may include, for example, but is not limited to, intramuscular, subcutaneous, intra-articular, and intraperitoneal administration. According to embodiments of the present disclosure, the administration may be intra-articular but is not limited thereto.

In the present disclosure, the individual includes any human or non-human animal. The term "non-human animal" may include vertebrates, such as non-human primates, sheep, dogs, and rodents, such as mice, rats, and guinea pigs. The subject may preferably be a human, and more specifically, a human having a particular disease. As used herein, the term " individual" may be used interchangeably with "subject" or "patient".

The references to the in-situ hybridization hydrogels, precursor compositions, methods of preparation, and methods of treatment of the present disclosure apply mutatis mutandis unless contradictory, and repetitions have been omitted to avoid undue complexity of the specification.

Advantageous Effects

The hydrogels of the present disclosure can locally and selectively capture and eliminate overproduced nitric oxide in and out of the body and thus have excellent preventive, alleviative or therapeutic effects in inflammatory diseases caused by overproduction of nitric oxide.

Furthermore, the hydrogels of the present disclosure can carry hydrophobic and/or hydrophilic drugs and thus can serve as a drug delivery system to the target site and can have a combined therapeutic effect of nitric oxide capture and drug delivery.

Furthermore, the hydrogels of the present disclosure can be degraded in response to nitric oxide, and thus, as the crosslinks dissociate in response to nitric oxide in the presence of nitric oxide, the drug carried in the hydrogel can be delivered locally and selectively to the target site.

Furthermore, the hydrogel of the present disclosure does not require surgical intervention and is minimally invasive, allowing for localized formation of the hydrogel at the targeted site, which is convenient for the patient.

In addition, the hydrogel of the present disclosure does not exhibit the problems of the previous technology, such as systemic toxicity, because it can be quickly removed from the target site and prevented from spreading to other organs.

In addition, the hydrogel of the present disclosure has excellent recovery of mechanical properties due to its self-healing ability and can be usefully used as a visco-supplement.

DESCRIPTION OF DRAWINGS

FIG. 4 shows whether the compound represented by Formula 1 can be degraded by reacting with nitric oxide;

Specifically.

FIG. 8 is FT-IR, GPC, TEM, and DLS data of the compound represented by Formula 2;

Specifically.

FIGS. 11 to 15 analyze the characteristics of the M-NO gel of the present disclosure;

Specifically.

FIGS. 16 and 17 show the reactivity and NO scavenging ability of the M-NO gel after LPS treatment of LPS-treated RAW 264.7 cells;

Specifically.

FIGS. 18 to 22 show the effectiveness of the M-NO gel of the present disclosure in treating rheumatoid arthritis in collagen-induced arthritis (CIA) mice, which is an animal model of rheumatoid arthritis;

Specifically.

FIG. 19 shows representative mouse hind paw images at 4, 6, and 8 weeks;

FIG. 21 shows the effectiveness of the M-NO gel of the present disclosure in treating rheumatoid arthritis in collagen-induced arthritis (CIA) mice, which is an animal model of rheumatoid arthritis;

Specifically.

FIG. 22**F shows quantification of NO levels in RA mouse paw tissue fluid treated with a week 8 sample. Data are presented as mean±SD (n=4), RA model mice treated with saline (B) were compared with other experimental groups and statistically analyzed using one-way ANOVA (*p<0.05, ***p<0.001; n.s. no significant difference).

MODE FOR INVENTION

The present disclosure is hereinafter described in more detail by way of embodiments. However, these embodiments are intended to illustrate the present disclosure by way of example, and the scope of the present disclosure is not limited by these embodiments. In addition, terms not specifically defined herein are to be understood to have the meanings commonly used in the art to which the present disclosure belongs.

Preparation Example 1. Synthesis of Compounds of Formula 1

Figure 1:
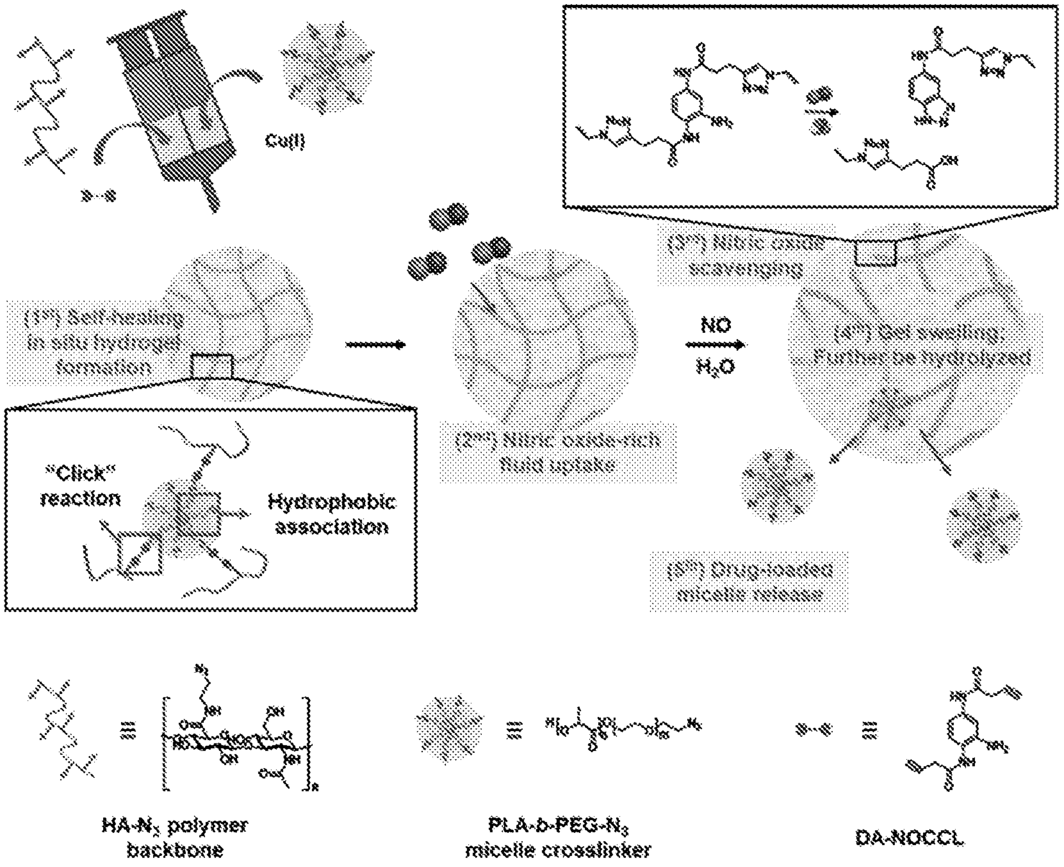
FIG. 1 is a schematic diagram of the hydrogel formation process of the present disclosure and the process of dissociation of crosslinking points in response to nitric oxide.
Figure 2:
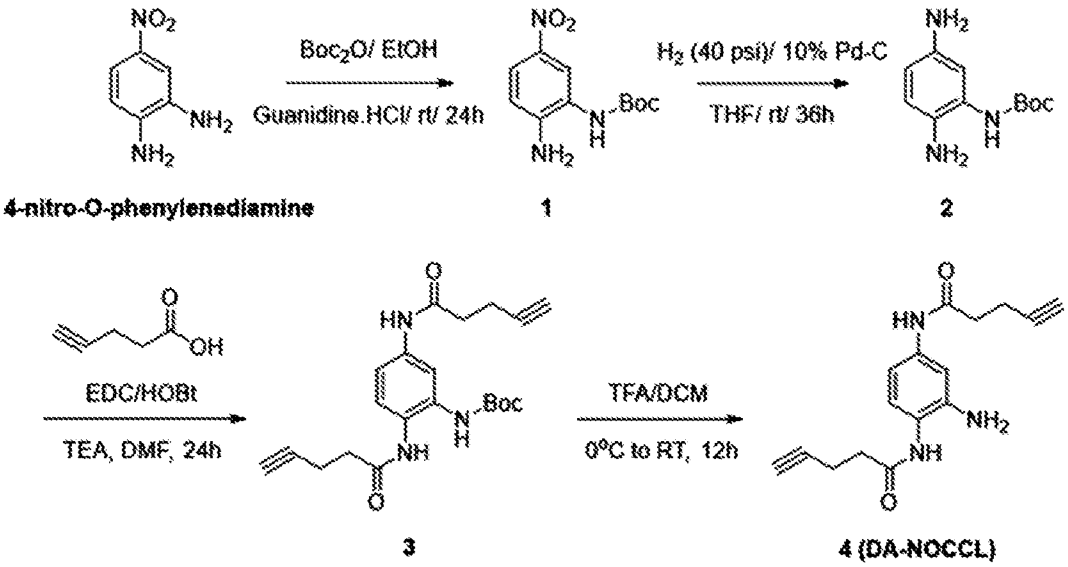
FIG. 2 shows the synthesis process of the compound represented by Formula 1.
Figure 3:
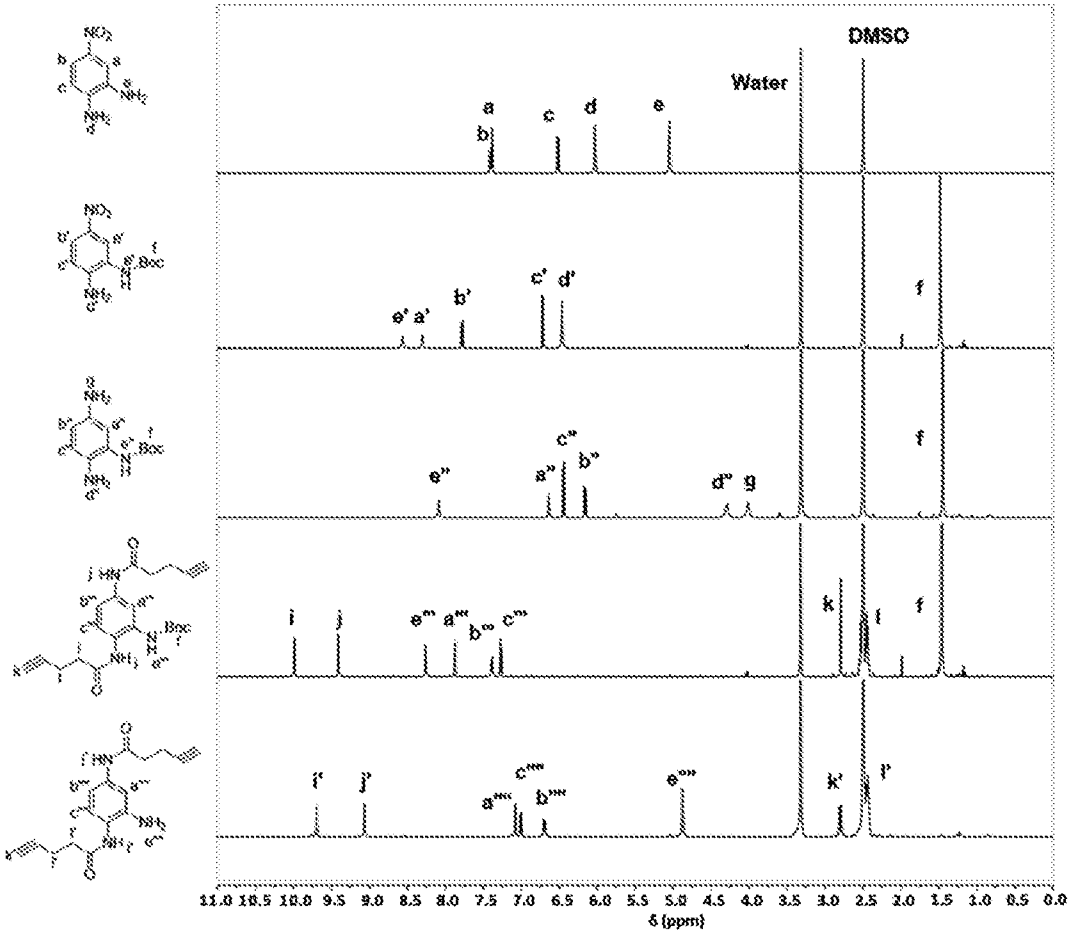
FIG. 3 is $^1$H NMR data of the compound obtained in each step of the synthesis of the compound represented by Formula 1.

For the synthesis of the nitric oxide-reactive, clickable crosslinking agent DA-NOCCL, the amine group at the C2 position of 4-nitro-o-phenylenediamine was first selectively Boc-protected using guanidine HCl as a catalyst. The 4-$NO_2$ was then reduced to 4-$NH_2$, and 4-pentynoic acid was bonded to each amine group via an amide bond. Subsequently, synthesis was completed by Boc-deprotection under acid conditions. The synthesis process of the crosslinking agent DA-NOCCL is shown in FIG. 2, and the successful synthesis of each compound obtained in the synthesis process and the crosslinking agent DA-NOCCL was confirmed by $^{1}$H NMR and shown in FIG. 3.

Each step of the specific synthesis is as follows.

Step 1: 4-Nitro-o-phenylenediamine (1 g, 6.53 mmol) and guanidine HCl (95 mg, 0.91 mmol) were dissolved in 20 ml of ethanol, di-tert-butyl dicarbonate (2.85 g, 13.06 mmol) was added dropwise, and the reaction mixture was stirred vigorously at 25° C. for 24 hours. After the reaction was completed, the organic solvent in the reaction solution was evaporated under reduced pressure and suspended in distilled water. The aqueous solution was extracted three times with ethyl acetate (EA), and the organic portion was washed with $Na_2SO_4$ to obtain a reddish yellow crude-solid, which was purified by silica gel column chromatography (eluent: EA-hexanes mixture) to obtain compound 1 (1.22 g, yield: 73.8%).

[Compound 1]

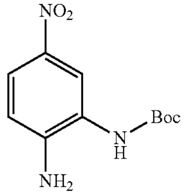

$^{1}$H NMR (500 MHz, DMSO-d6): δ=8.56 (brs, 1H, $D_2O$ exchangeable), 8.30 (d, J=1.6 Hz, 1H), 7.78 (dd, J=9.0, 2.7 Hz, 1H), 6.72 (d, J=9.0 Hz, 1H), 6.46 (brs, 2H, $D_2O$ exchangeable), 1.48 (s, 9H).

Step 2: After the addition of activated carbon (10% Pd/C) loaded with 100 mg of palladium to a solution of compound 1 (400 mg, 1.58 mmol) in 10 ml anhydrous THF under nitrogen, hydrogen gas was pumped until the pressure reached a maximum of 40 psi, and the reaction mixture was stirred at 25° C. for 36 hours. After completion of the reaction, the reaction mixture was filtered through a bed of Celite 545 to remove Pd/C and evaporated under reduced pressure to obtain purple solid compound 2 (322 mg, yield: 91.2%).

[Compound 2]

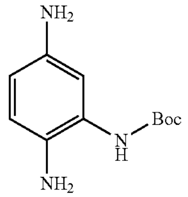

$^{1}$H NMR (500 MHz, DMSO-d6): δ=8.08 (brs, 1H, $D_2O$ exchangeable), 6.64 (d, J=1.6 Hz, 1H), 6.45 (d, J=8.3 Hz, 1H), 6.16 (dd, J=8.3, 2.5 Hz, 1H), 4.29 (brs, 2H, $D_2O$ exchangeable), 4.01 (brs, 2H, $D_2O$ exchangeable), 1.45 (s, 9H).

Step 3: Compound 2 (200 mg, 0.90 mmol), 4-pentynoic acid (200 mg, 2.04 mmol), HOBt (280 mg, 2.07 mmol), and triethylamine (TEA, 190 mg, 1.88 mmol) were completely dissolved in 10 ml of anhydrous DMF. EDC (400 mg, 2.09 mmol) was added to the solution, and the reaction mixture was stirred vigorously at 25° C. for 24 hours. After completion of the reaction, the reaction mixture was evaporated under reduced pressure and suspended in $CH_2Cl_2$. The organic solvent was extracted three times with distilled water, and the organic portion was washed with $Na_2SO_4$ to obtain a light brown crude-solid, which was purified by silica gel column chromatography (eluent: EA-hexanes mixture) to obtain compound 3 (285 mg, 0.74 mmol, yield: 82.7%).

[Compound 3]

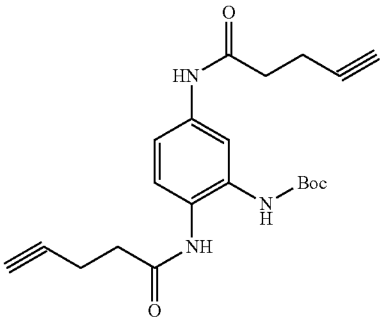

$^{1}$H NMR (500 MHz, DMSO-d6): δ=9.99 (brs, 1H, $D_2O$ exchangeable), 9.41 (brs, 1H, $D_2O$ exchangeable), 8.26 (brs, 1H, $D_2O$ exchangeable), 7.87 (d, J=2.2 Hz, 1H), 7.39 (dd, J=8.7, 2.2 Hz, 1H), 7.27 (d, J=8.7 Hz, 1H), 2.79 (t, J=2.5 Hz, 2H), 2.55-2.41 (m, 8H), 1.47 (s, 9H).

Step 4: 5 ml of trifluoroacetic acid (TFA) was added dropwise to compound 3 (200 mg, 0.52 mmol) suspended in 20 ml $CH_2Cl_2$ at 0° C. The reaction mixture was then stirred vigorously at 25° C. for 12 hours. After completion of the reaction, the reaction mixture was evaporated under reduced pressure and neutralized with saturated sodium bicarbonate ($NaHCO_3$) solution. The neutralized solution was extracted three times with 5% (v/v) methanol in $CH_2Cl_2$, and the organic portion was washed with $Na_2SO_4$ to obtain the cross-linking agent DA-NOCCL (138 mg, 0.49 mmol, yield: 93.5%).

[DA-NOCCL]

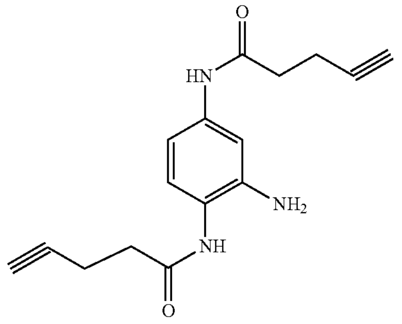

$^1$H NMR (500 MHz, DMSO-d6): δ=9.70 (brs, 1H, $D_2O$ exchangeable), 9.06 (brs, 1H, $D_2O$ exchangeable), 7.08 (d, J=2.2 Hz, 1H), 7.01 (d, J=8.5 Hz, 1H), 6.70 (dd, =8.5, 2.2 Hz, 1H), 4.88 (brs, 2H, $D_2O$ exchangeable), 2.78 (dt, J =14.7, 2.4, 2H), 2.44 (m, 8H).

Figure 4A:
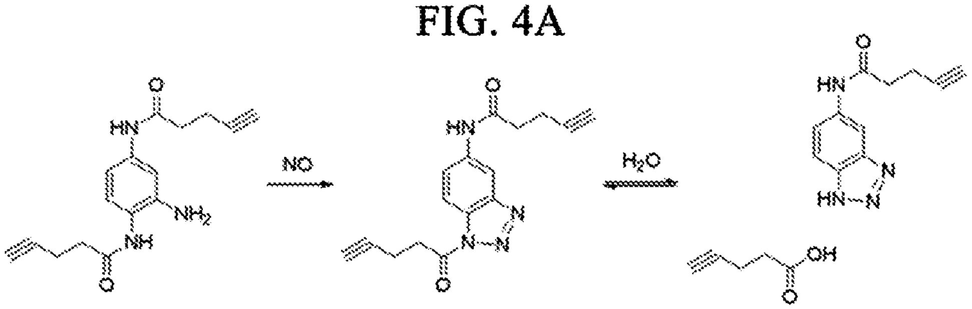
FIG. 4A shows a mechanism in which the compound represented by Formula 1 reacts with nitric oxide to degrade.
Figure 4B:
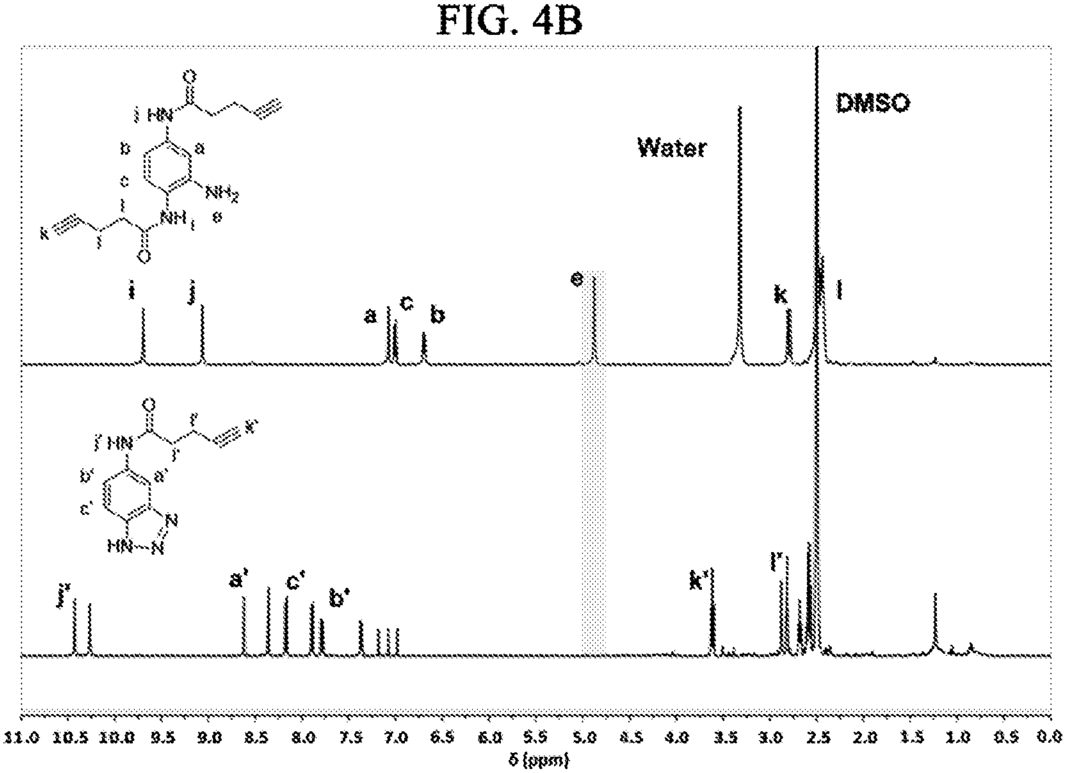
FIG. 4B shows $^1$H NMR data confirming whether the compound represented by Formula 1 is degraded by reaction with nitric oxide.
Figure 5A:
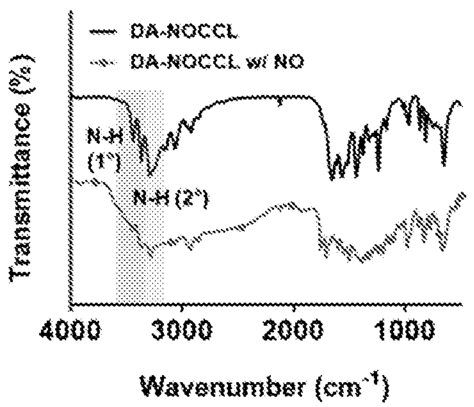
FIG. 5 shows FT-IR (a) and UV-Vis absorption data (b) confirming whether the compound represented by Formula 1 is degraded by reaction with nitric oxide.
Figure 5B:
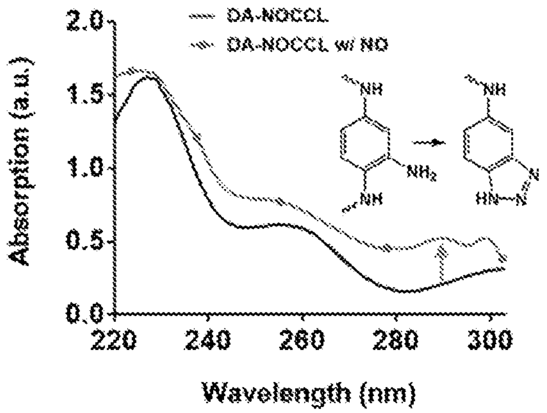

The mechanism by which the above synthesized cross-linking agent DA-NOCCL reacts with nitric oxide to degrade and the $^1$H NMR, FT-IR, and UV-Vis absorption data confirming this are shown in FIGS. 4 and 5.

As can be seen in FIGS. 4 and 5, after incubation in a saturated NO solution, the characteristic peak of the primary amine disappeared, and a benzotriazole group was formed, confirming that the crosslinking agent DA-NOCCL can be degraded in response to NO.

Preparation Example 2. Synthesis of Compounds of Formula 2

Figure 6:
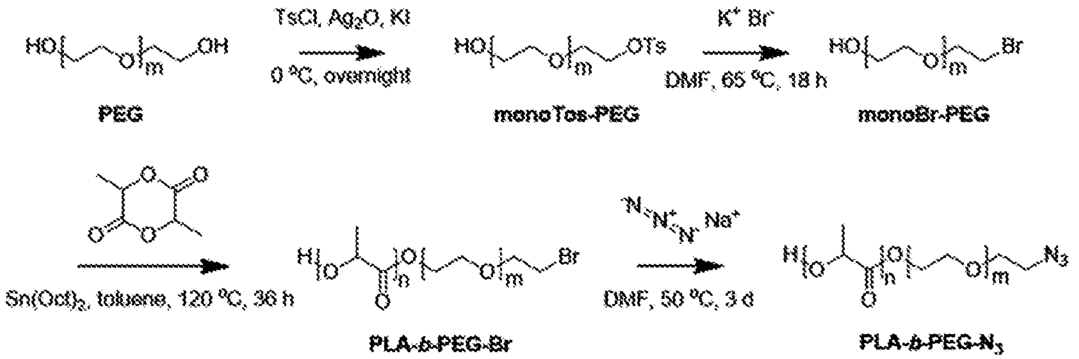
FIG. 6 shows the synthesis process of the compound represented by Formula 2.
Figure 7:
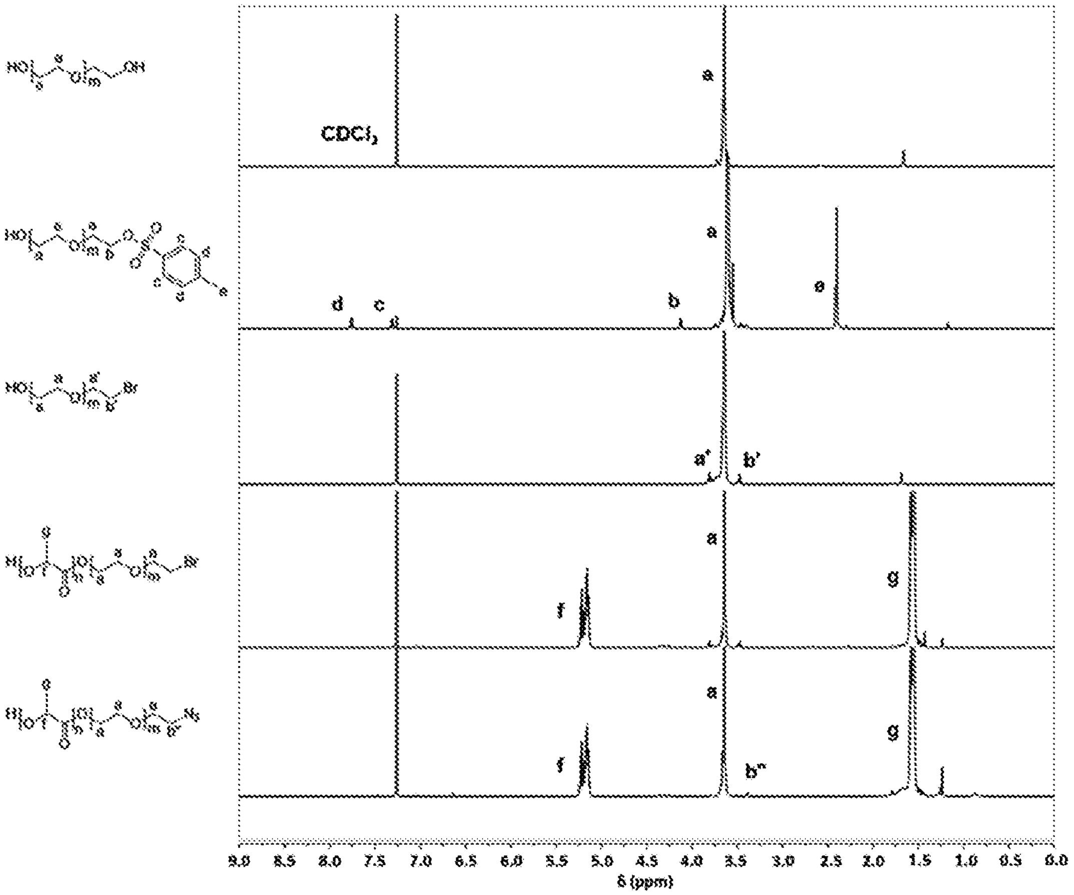
FIG. 7 is $^1$H NMR spectrum data of the compound obtained in each step of the synthesis of the compound represented by Formula 2.
Figure 8A:
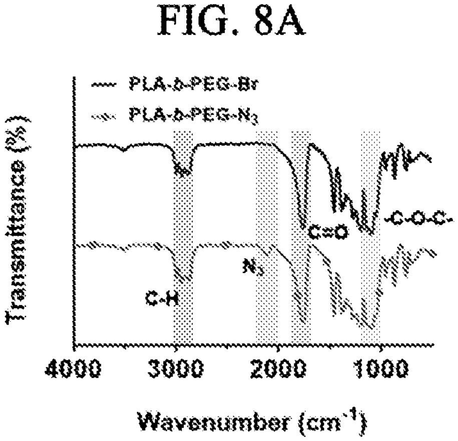
FIG. 8A shows FT-IR spectrum data of PLA-b-PEG-N3.
Figure 8B:
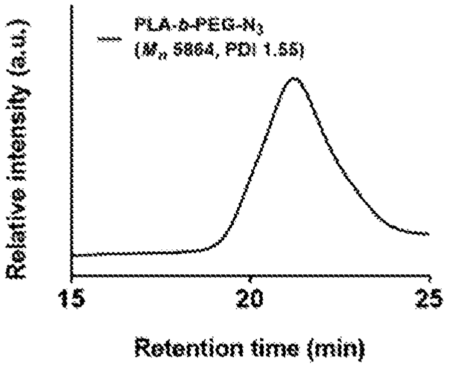
FIG. 8B shows gel permeation chromatography (GPC) data of PLA-b-PEG-N3.

For the synthesis of the crosslinking agent represented by Formula 1 and the clickable compound of Formula 2, polyethylene glycol (PEG) was used as a starting material, and one of the hydroxyl groups of PEG was selectively tosylated under silver oxide ($Ag_2O$) catalyzed conditions, followed by the substitution of the tosyl group with bromide. The formed PEG-Br was then ring-linked polymerized with D,L-lactide to form a block copolymer of PLA-b-PEG-Br. Finally, the synthesis was completed by replacing the bromide group with azide. After dissolving 10 mg of the synthesized PLA-b-PEG-N3 in 1 ml of THF, 9 ml of water was added dropwise to form a micelle structure, and the remaining THF was removed through dialysis. Each step of the specific synthesis is as follows, and the synthesis process is shown in FIG. 6. The successful synthesis of PLA-b-PEG-N3 was confirmed by $^1$H NMR, FT-IR, and GPC, and is shown in FIGS. 7, 8A, and 8B, respectively.

Each step of the specific synthesis is as follows.

Step 1: Silver(I) oxide (1.74 g, 7.51 mmol) and potassium iodide (KI, 0.33 g, 1.99 mmol) were added to a vacuum-dried solution of 2 kDa PEG (10 g, 5.00 mmol) dissolved in 160 ml anhydrous dichloromethane ($CH_2Cl_2$), p-toluene sulfonyl chloride (TsCl, 1 g, 5.25 mmol) in 20 ml anhydrous $CH_2Cl_2$ was added and stirred vigorously at 0° C. overnight. After completion of the reaction, the reaction mixture was carefully filtered through a Celite 545 bed and evaporated under reduced pressure to obtain a colorless oily product. The obtained product was further purified through multiple $CH_2Cl_2$/diethyl ether ($(C_2H_5)_2O$) recrystallization to obtain a white solid precipitate (monoTos-PEG, 9.72 g, yield: yield: 90.9%).

Step 2: Both monoTos-PEG (4.0 g, 1.86 mmol) and potassium bromide (KBr, 1.1 g, 9.24 mmol) were dissolved in 40 ml of anhydrous dimethylformamide (DMF) and reacted at 65° C. for 18 hours under stirring. After completion of the reaction, the reaction mixture was evaporated under reduced pressure and redispersed in $CH_2Cl_2$. The obtained product was passed through short silica gel and further purified via multiple $CH_2Cl_2/(C_2H_5)_2O$ recrystallization to give a white solid precipitate (monoBr-PEG, 3.59 g, yield: yield: 93.5%).

Step 3: MonoBr-PEG (1.5 g, 0.72 mmol) and 3,6-dimethyl-1,4-dioxane-2,5-dione (D,L-lactide, 2.1 g, 14.57 mmol) were dissolved in 5 ml of anhydrous toluene. After performing several freeze-thaw cycles to the solution, polymerization was initiated by adding a tin(II) 2-ethylhexanoate catalyst ($Sn(Oct)_2$, 0.01 g, 0.02 mmol). The reaction mixture was then stirred vigorously at 120° C. for 36 hours. After completion of the reaction, the reaction mixture was evaporated under reduced pressure and redispersed in $CH_2Cl_2$. The product was purified through multiple $CH_2Cl_2/(C_2H_5)_2O$ recrystallization to obtain a white amorphous solid precipitate. The obtained product was further purified (PLA-b-PEG-Br) by 2-day dialysis in distilled water and subsequent lyophilization. The molecular weight was determined by gel permeation chromatography (GPC) in tetrahydrofuran (THF) (Mn=5540, PDI=1.50).

Step 4: The above prepared PLA-b-PEG-Br (1.1 g, 0.19 mmol) and excess sodium azide ($NaN_3$, 0.45 g, 6.92 mmol) were dissolved in 20 ml of anhydrous DMF, and the reaction mixture was stirred vigorously at 50° C. for 3 days. After completion of the reaction, the product was purified (PLA-b-PEG-N3) by 2-day dialysis in distilled water and subsequent lyophilization. The molecular weight was determined by GPC in THF (Mn=5864, PDI=1.55).

Figure 8C:
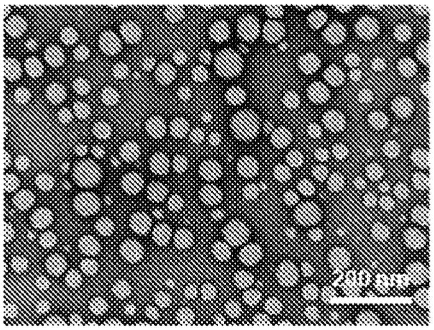
FIG. 8C shows a transmission electron microscope (TEM) image of PLA-b-PEG-N3.
Figure 8D:
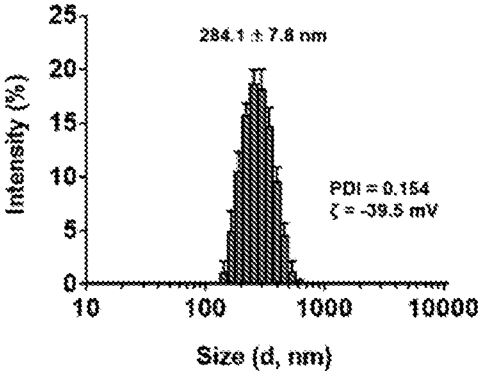
FIG. 8D shows the average hydrodynamic size determined by dynamic light scattering spectroscopy (DLS) of PLA-b-PEG-N3.

Furthermore, the TEM and DLS data of the micelle structures formed by the self-assembly of the above-prepared PLA-b-PEG-N3 were shown in FIGS. 8C and 8D, respectively, which confirmed that PLA-b-PEG-N3 could self-assemble under aqueous conditions to form uniform micelle structures with a size of about 284.1±7.8 nm.

Preparation Example 3. Synthesis of Compounds of Formula 3

Figure 9A:
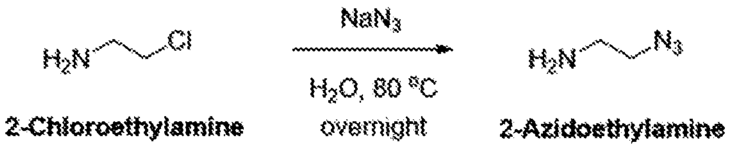
FIG. 9 shows the synthesis process of the compound represented by Formula 3.
Figure 9B:
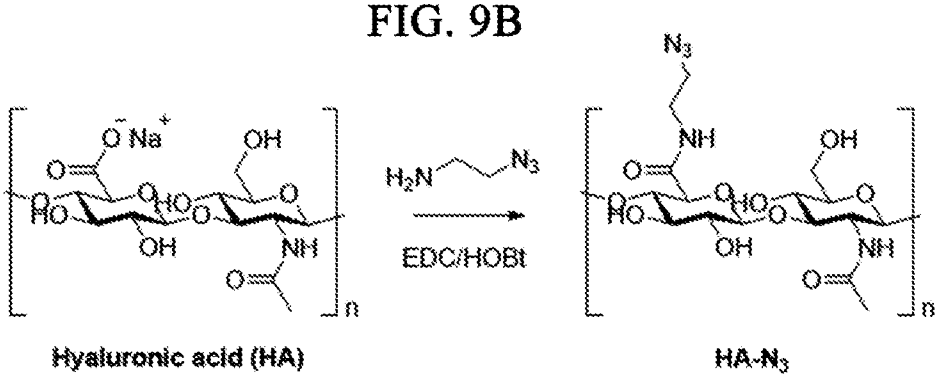
Figure 10A:
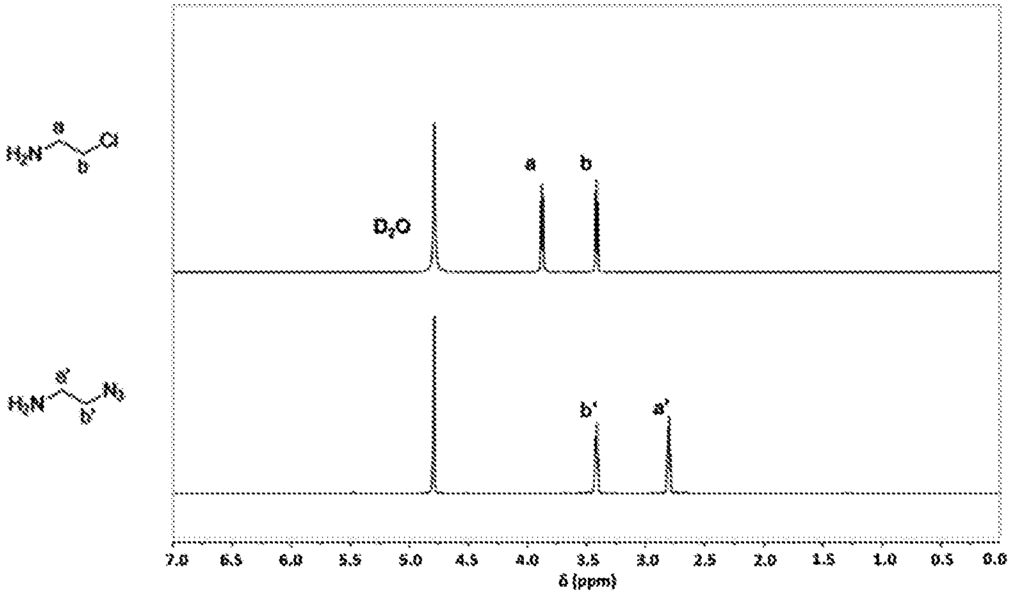
FIG. 10 is $^1$H NMR spectrum data of the compound obtained in the process of synthesizing the compound represented by Formula 3.
Figure 10B:
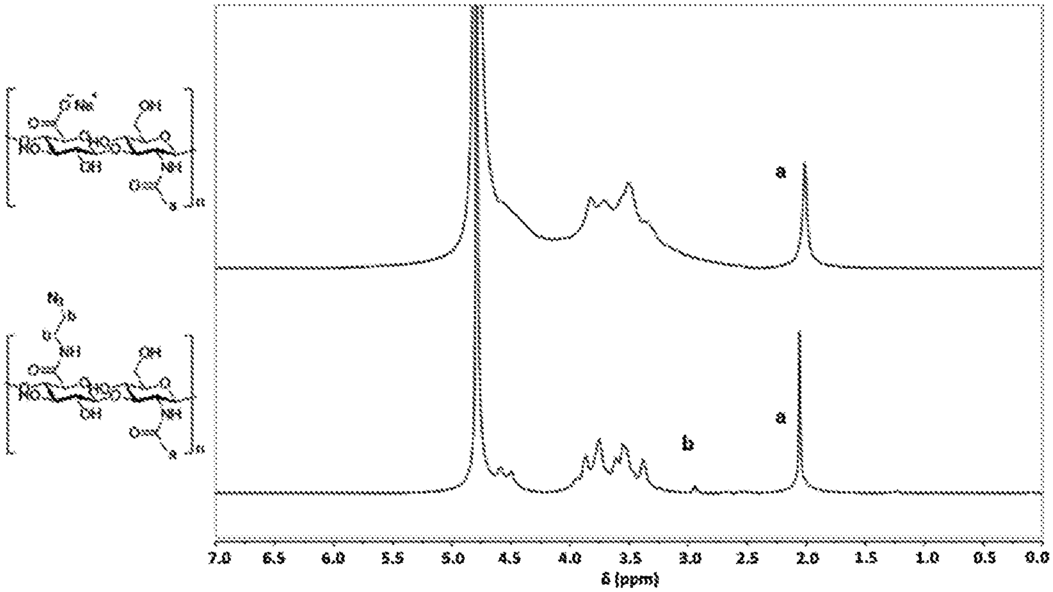

The hyaluronic acid-based polymer chain (HA-N3), which is a compound represented by Formula 1 and a compound represented by Formula 3 that can be clicked to form a hydrogel backbone, was synthesized by replacing the chloride group of 2-chloroethylamine with an azide group and then bonding the substituted 2-azidoethylamine with hyaluronic acid via an amide bond. The synthesis process of the above hyaluronic acid-based polymer chains is shown in FIG. 9, and the corresponding $^1$H NMR spectra of the compounds obtained at each step of the synthesis are shown in FIG. 10.

Each step of the specific synthesis is as follows.

Step 1: Both 2-chloroethylamine hydrochloride (1.16 g, 10.00 mmol) and $NaN_3$ (1.3 g, 20.00 mmol) were dissolved in 30 ml distilled water, and the reaction mixture was stirred vigorously at 80° C. for 12 hours. After completion of the reaction, 1 M sodium hydroxide (NaOH) solution was added to adjust the pH of the solution to 10 to 11. The alkaline solution was extracted three times with $CH_2Cl_2$ and the organic portion was washed with anhydrous sodium sulfate ($Na_2SO_4$) to obtain a pale yellow oily product (2-azidoethylamine, 0.62 g, yield: yield: 72.0%).

$^1H$ NMR (500 MHz, $D_2O$): δ=3.41 (t, J=5.7Hz, 1H), 2.80 (t, J=5.7Hz, 1H).

Step 2: 100 kDa hyaluronic acid (HA, 200 mg, 0.50 mmol (repeat unit)) was completely dissolved in 40 ml of distilled water, and in this solution N-(3-dimethylaminopropyl)-N'-ethylcarbodiimide hydrochloride (EDC, 144 mg, 0.75 mmol), 1-hydroxybenzotriazole (HOBt, 101 mg, 0.75 mmol), and 2-azidoethylamine (51.7 mg, 0.60 mmol) were added. After adjusting the pH to 6.8, the reaction mixture was vigorously stirred at 25° C. for 1 day in the dark. After completion of the reaction, the product was purified by continuous dialysis in 0.1 M sodium chloride (NaCl) and distilled water and lyophilized to obtain HA-N3.

Preparation Example 4. Preparation of Hydrogel

The nitric oxide-sensitive hydrogel (hereinafter referred to as M-NO gel) of the present disclosure was prepared through the following method.

Specifically, the M-NO gel was prepared using a dual syringe system. One syringe of the dual syringe system included the compounds represented by Formulae 1 and 3, and the other syringe included the compound represented by Formula 2 and the Cu(I) catalyst. The syringes including Formula 1 and Formula 3 were prepared in 1% (v/v) DMSO at concentrations of 0.04% by weight and 2.5% by weight, respectively. Syringes containing the compound represented by Formula 2 and the Cu(I) catalyst were prepared in distilled water, with concentrations of 2% by weight and 0.02% by weight, respectively. Here, the Cu(I) catalyst was prepared by mixing 15.5 mg of $CuSO_4$-$5H_2O$ and 22.0 mg of sodium ascorbate in 0.2 mL of distilled water.

In addition, the nitric oxide non-reactive hydrogel used as a control group was prepared by replacing DA-NOCCL with DA-NONCL (dialkyne-functionalized non-cleavable cross-linking agent) in the above method of preparation of M-NO gel.

Experimental Example 1 Morphological Analysis of M-NO Gels

Figure 11A:
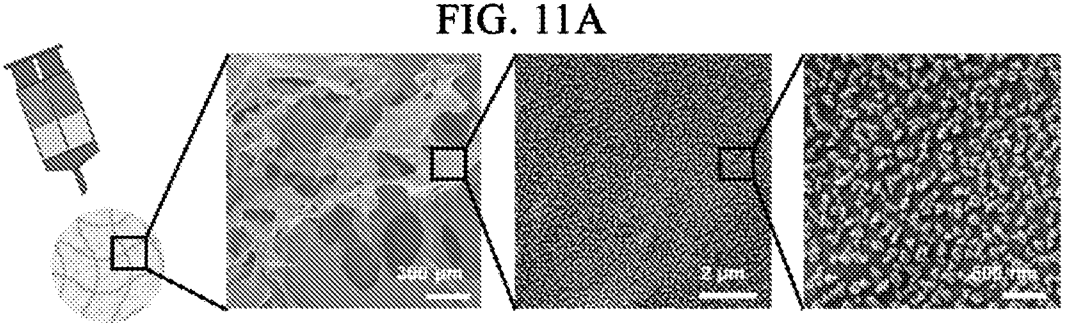
FIG. 11A is an image of the M-NO gel through cryogenic scanning electron microscopy.

For morphological analysis of the M-NO gel of the present disclosure, the M-NO gel prepared with a dual syringe system was imaged through cryogenic scanning electron microscopy, which is shown in FIG. 11A.

As can be seen in FIG. 11A, the micelle structures are uniformly distributed and fixed within the network structure hydrogel.

Experimental Example 2 Mechanical Characterization of M-NO Gels

In order to confirm the use of the M-NO gels of the present disclosure as artificial visco-supplements for joints, the self-healing properties of the M-NO gels after rupture were analyzed by dynamic transient test.

Figure 11B:
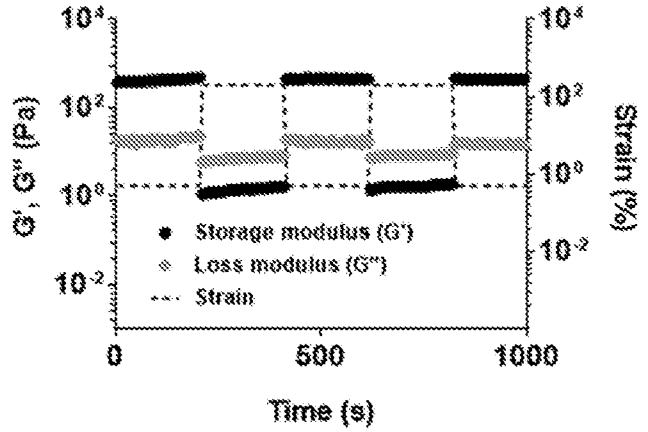
FIG. 11B shows the vibrational rheological characteristics of self-healing M-NO gel through a dynamic transient test.
Figure 12A:
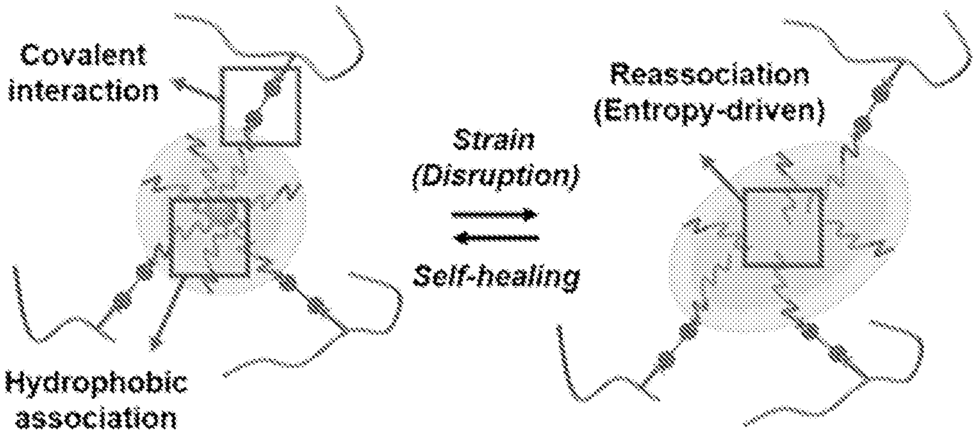
FIG. 12A shows a schematic diagram of self-healing of M-NO gel.

Specifically, the step-strain over several cycles (ε=0.5 to 200%, ωrad/s, 25° C.) was measured to determine the self-healing effect of the mechanical properties after rupture of the network structure at high strain, which is an important parameter of the artificial visco-supplement, and the results are shown in FIGS. 11B and 12A.

As can be seen from the above results, the M-NO gel exhibited almost complete recovery following stress-induced flow, confirming that the M-NO gel of the present disclosure can be useful as a visco-supplement.

Experimental Example 3 Analysis of NO Concentration-Dependent Changes in Mechanical Properties of M-NO Gels Frequency-dependent rheological parameters were analyzed to confirm the change in mechanical properties according to the NO concentration of the M-NO gel.

Figure 12B:
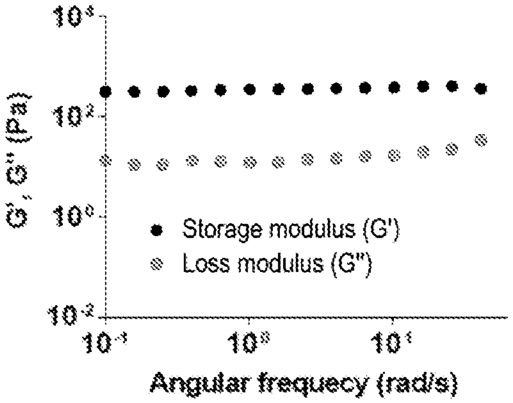
FIG. 12B shows the frequency-dependent vibrational rheological properties of M-NO gel.
Figure 12C:
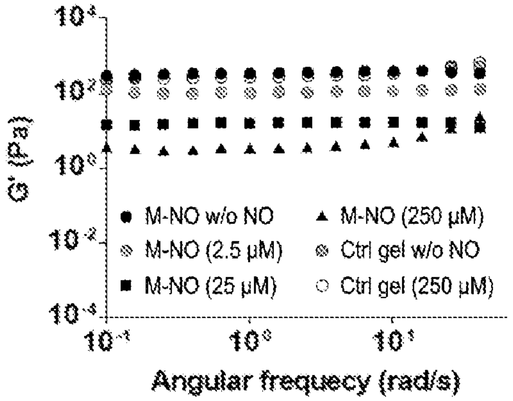
FIG. 12C shows NO concentration-dependent vibrational rheological properties of M-NO gel and control group gel (non-reactive to NO)
Figure 13A:
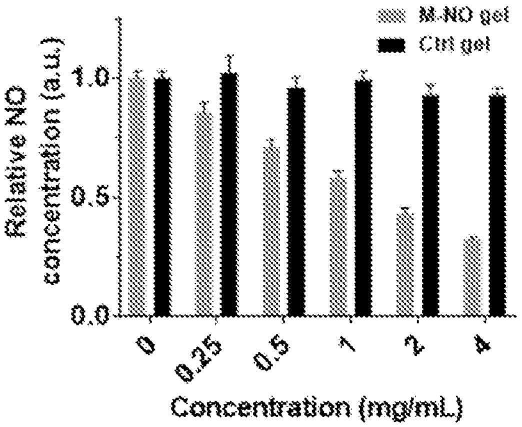
FIG. 13A confirms the NO scavenging ability of M-NO gel; Data are expressed as mean±SD (n=4)
Figure 13B:
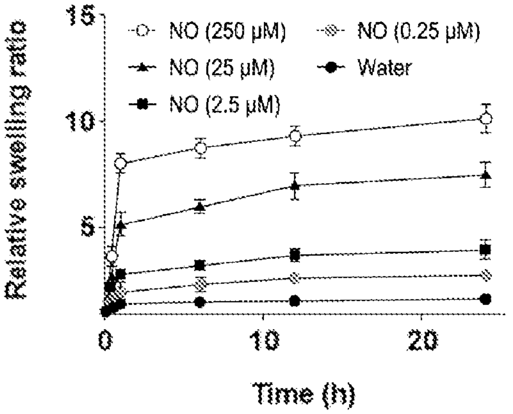
FIG. 13B shows the relative swelling ratio of M-NO gels over time at various concentrations; Data are expressed as mean±SD (n=4)
Figure 13C:
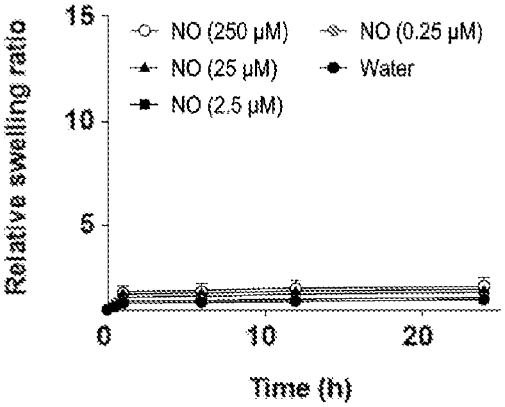
FIG. 13C shows the relative swelling ratio of the control group gel (non-reactive to NO) over time at various concentrations; Data are expressed as mean±SD (n=3)
Figure 13D:
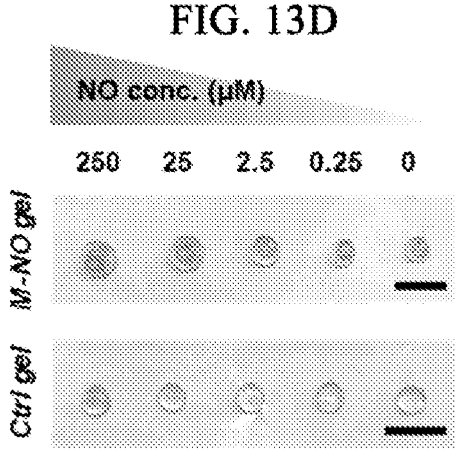
FIG. 13D shows images of M-NO gel and control group gel (non-reactive to NO) after incubation in NO solutions of various concentrations for 2 hours; scale bar is 1 cm.

Specifically, the frequency-dependent vibrational rheological properties (ε%, 25° C.) and concentration-dependent rheological properties (ωrad/s at ωrad/s, ε%, 25° C.) of the NO non-reactive gel and the NO-reactive M-NO gel of the present disclosure were compared by measuring and quantifying the angular frequency, and the results are shown in FIGS. 12B and 12C.

As shown in FIGS. 12B and 12C, the storage modulus of the NO-reactive M-NO gel decreased progressively with the concentration of NO, indicating a decrease in mechanical strength upon NO-mediated degradation of the crosslinking agent, whereas the control group, the NO non-reactive gel, did not show any significant change in the storage modulus even at high concentrations of NO solution. That is, it was confirmed that the M-NO gel of the present disclosure exhibited a degradation pattern according to an increase in NO concentration.

Experimental Example 4 Confirmation of NO Scavenging Ability of M-NO Gel

The NO scavenging ability of the M-NO gel of the present disclosure was determined after preparing a 25 μM Py-NO solution using a synthesized NO donor Py-NO (N-diazeniumdiolates-incorporated pyrrolidine), which can release NO under aqueous conditions, M-NO gels and NO non-reactive gels were treated with the above-prepared 25 μM Py-NO solution, incubated for 1 hour, and the residual NO levels in the supernatant were quantified by grease assay (absorbance at 548 nm was compared to a standard curve plotted with $NaNO_2$ to determine NO concentration). Furthermore, the swelling level of the hydrogel was measured and confirmed, and the relative swelling ratio was calculated using the following Formula, and the results are shown in FIGS. 13A, 13B, 13C, and 13D.

<Formula>

–Expansion ratio=(Mf–Mi)/Mi (Mf: Weight of hydrogel swollen in NO solution, Mi: Weight of dried hydrogel)

Relative expansion ratio=expansion ratio/expansion ratio by water at 0 *h*

As can be seen in FIGS. 13A, 13B, 13C, and 13D, the M-NO gels of the present disclosure significantly reduced the amount of NO solution as a function of the concentration of NO and swelled significantly compared to the control group, NO non-reactive gel.

In other words, the M-NO gel of the present disclosure effectively eliminates nitric oxide in a concentration-dependent manner and has swelling properties due to an increase in pore size by cleavage of the network structure of the hydrogel depending on the NO concentration, thus enabling on-demand controlled delivery according to the NO concentration.

Experimental Example 5 Confirmation of Simultaneous Dual Drug Release of M-NO Gels The NO-reactive simultaneous dual-stage drug release of M-NO gel was confirmed by the following experiments.

Specifically, a hydrophilic drug model, fluorescein isothiocyanate-labeled bovine serum albumin (BSA-FITC), was encapsulated into the hydrophilic domain of the hydrogel by dissolving it in a solution containing HA-N3 to a final concentration of 1% by weight, and a hydrophobic drug model, Nile Red, was encapsulated into the hydrophobic domain of PLA-b-PEG-N3 micelles. The hydrophilic and hydrophobic drug models were co-encapsulated in M-NO gel upon hydrogel formation.

Then, 200 μL of M-NO gel was incubated in 5 mL of NO solution (0, 2.5, 25, and 250 μM) at 25° C. The supernatant was replaced with NO solution at predetermined time intervals, the obtained supernatant was concentrated by lyophilization, and the time-dependent NO-reactive simultaneous dual drug release profiles of BSA-FITC and Nile red were investigated by comparing the fluorescence (excitation/emission peaks were 485/510 nm) and absorbance at 585 nm with standard curves.

Figure 14A:
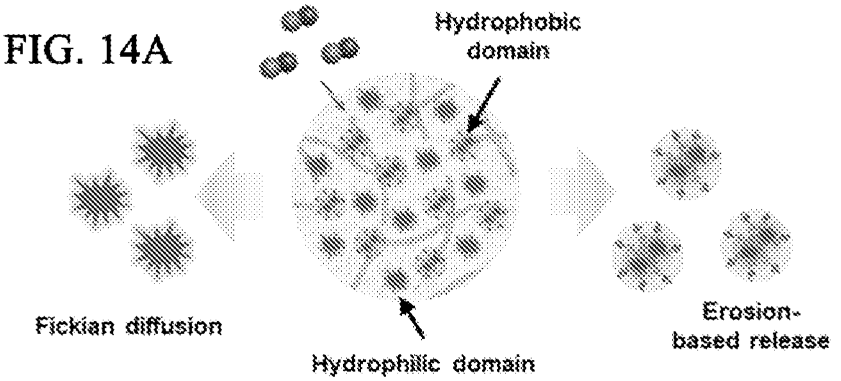
FIG. 14A shows a schematic diagram of simultaneous dual drug release in M-NO gel.
Figure 14B:
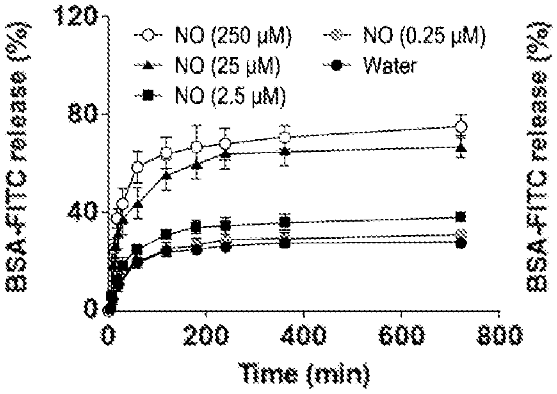
FIG. 14B shows the hydrophilic cargo model (BSA-FITC) release profile of M-NO gel.

A schematic diagram of the dual drug release is shown in FIG. 14A, and the results are shown in FIGS. 14B, 14C, 14D, and 14E.

Figure 14C:
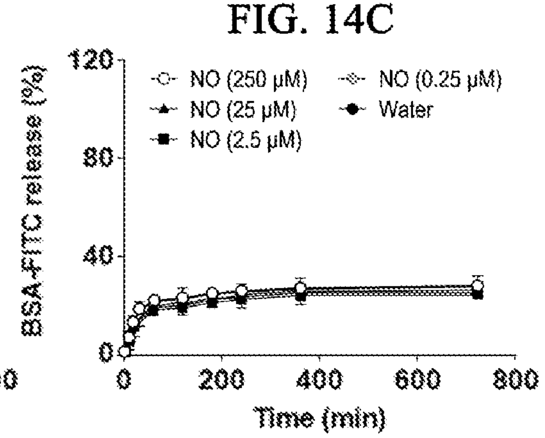
FIG. 14C shows the BSA-FITC release profile of the control group gel.
Figure 14D:
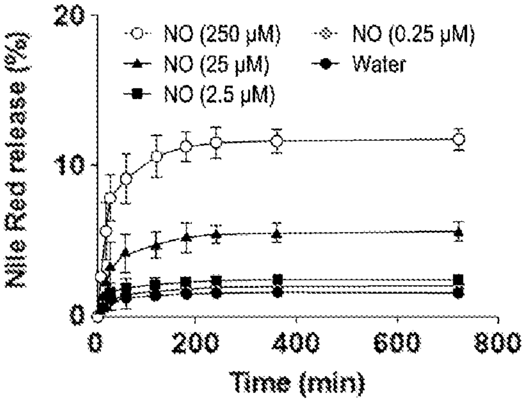
FIG. 14D shows the hydrophobic cargo model (Nile Red) release profile carried on the micelle structure of M-NO gel.
Figure 14E:
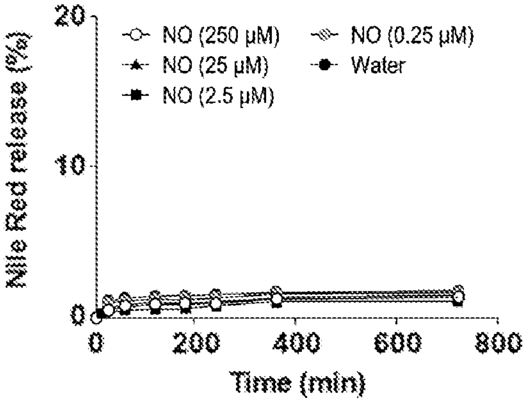
FIG. 14E shows the Nile Red release profile of the control group gel.

As can be seen in FIGS. 14B, 14C, 14D, and 14E, the M-NO gel of the present disclosure was able to rapidly release both hydrophilic molecules with release characteristics due to Fickian diffusion and hydrophobic molecules with release characteristics due to an erosion-based mechanism at high NO concentrations (FIGS. 14B and 14D), but the NO non-reactive gel as a control group did not show any particular release behavior despite the increase in NO concentration (FIGS. 14C and 14E).

Figure 15A:
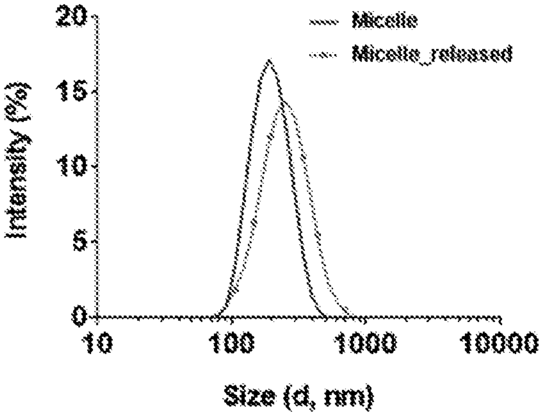
FIG. 15A shows the average hydrodynamic size of PLA-b-PEG-N3 micelle structures before hydrogel formation and the average hydrodynamic size of PLA-b-PEG-N3 micelle structures identified in the supernatant after incubation of M-NO gels with NO solution (250 μM) for 24 hours.
Figure 15B:
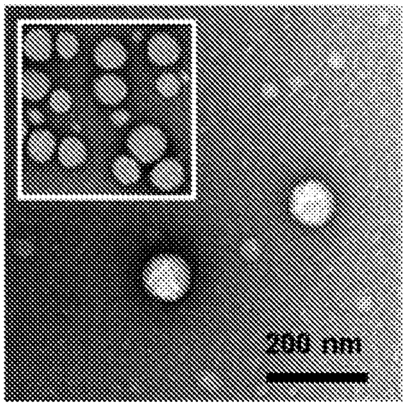
FIG. 15B shows a TEM image of the supernatant after erosion of the M-NO gel; the white box in the image represents the morphology of the micelle structure before gel formation.

Furthermore, whether erosion-based release of hydrophobic drugs from the micelle structures of the M-NO gel of the present disclosure is possible was determined by comparing the average hydrodynamic size of the PLA-b-PEG-N3 micelle structures before hydrogel formation with the average hydrodynamic size of the PLA-b-PEG-N3 micelle structures found in the supernatant after incubation of the M-NO gel with NO solution (250 μM) for 24 hours, and the results are shown in FIGS. 15A and 15B.

As shown in FIGS. 15A and 15B, micelle structures with hydrodynamically similar size and morphology to the PLA-b-PEG-N3 micelle structures before hydrogel formation were observed in the supernatant of M-NO gels incubated with NO solution, confirming that hydrophobic drugs can be released by an erosion-based mechanism.

Experimental Example 6 Confirmation of Cytotoxicity of M-NO

The dose-dependent cytotoxicity of M-NO of the present disclosure and the control group was confirmed through an MTT assay.

Specifically, RAW 264.7 cells were inoculated into 96-well plates at an initial density of $1\times10^4$ cells/well and incubated in DMEM medium containing 10% FBS, 100 U/mL penicillin, and 100 μg/mL streptomycin at 37° C.

After 24 hours of incubation, the medium was replaced with a fresh medium containing the sample and incubated again for 40 hours. The cells were then washed and incubated in a medium containing 0.5 mg/mL of MTT solution for 4 hours. Finally, the medium was replaced with 200 μL DMSO, and cell viability was examined by measuring absorbance at 570 nm, the results of which are shown in FIG. 16B.

Figure 16A:
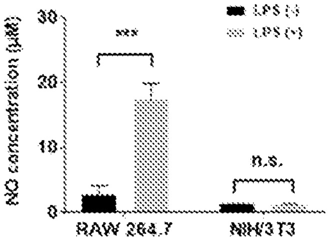
FIG. 16A shows NO concentrations before and after 24-hour treatment of RAW 264.7 and NIH/3T3 cell lines with 5 μg/ml LPS.
Figure 16B:
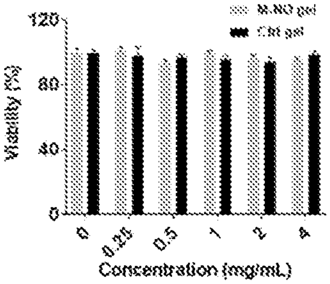
FIG. 16B shows the cell viability of RAW 264.7 cell line treated with various concentrations of M-NO gels and control group gels; data are expressed as mean±SD (n=5)

As can be seen in FIG. 16B, the M-NO gel of the present disclosure has little effect on cell viability, confirming the safety of the M-NO of the present disclosure.

Experimental Example 7 Confirmation of NO Scavenging Ability of M-NO

The NO-scavenging ability of the compositions of the present disclosure and the resulting cytokine levels were determined using the NO-releasing RAW 264.7 macrophage cell line stimulated with LPS.

(1) Confirmation of NO Scavenging Ability According to Concentration

The RAW 264.7 cell line was inoculated into 12-well plates at a density of $5\times10^4$ cells/well and incubated in DMEM medium containing 10% FBS, 100 U/mL penicillin, and 100 μg/mL streptomycin at 37° C.

After incubation overnight, the medium was replaced with fresh medium containing 5 μg/mL of LPS, including the sample, and incubated again for 24 hours.

Figure 16C:
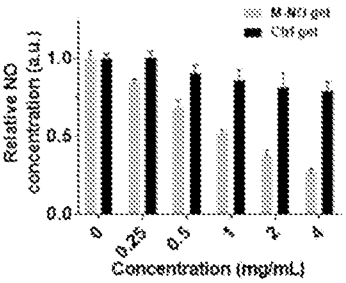
FIG. 16C shows the NO scavenging ability of the M-NO gel, where different concentrations of the M-NO gel were treated on the RAW 264.7 cell line, and the level of NO in the cell medium supernatant after 24 hours of incubation was determined by Griess assay.

Finally, the medium was centrifuged (3,000 rpm, 10 min, 4° C.) to obtain the supernatant, which was then transferred to a 96-well plate, and the level of NO remaining in the supernatant was determined by grease analysis, which is shown in FIG. 16C.

As can be seen in FIG. 16C, it can be confirmed that the M-NO gel of the present disclosure can significantly reduce the NO levels of the LPS-stimulated RAW 264.7 cell line by 25%, which is similar to the values observed in untreated RAW 264.7.

(2) Confirmation of NO Scavenging Ability Through Confocal Microscopy

Intracellular NO levels were imaged by confocal microscopy to assess NO scavenging ability.

Specifically, cells were inoculated into cover glasses placed in a 6-well plate at a density of $1\times10^5$ cells/well and incubated in DMEM medium containing 10% FBS, 100 U/mL penicillin, and 100 μg/mL streptomycin at 37° C.

After incubation overnight, the medium was replaced with fresh medium containing 5 μg/mL of LPS with samples (25 μg/mL for crosslinking agent and 250 μg/mL for gel) and incubated again for 24 hours.

The sample medium was then replaced with fresh medium containing 5 pm DAF-2 DA and incubated again for 40 min, after which the cells were washed with DPBS and incubated with fresh medium for another 20 min.

Figure 16D:
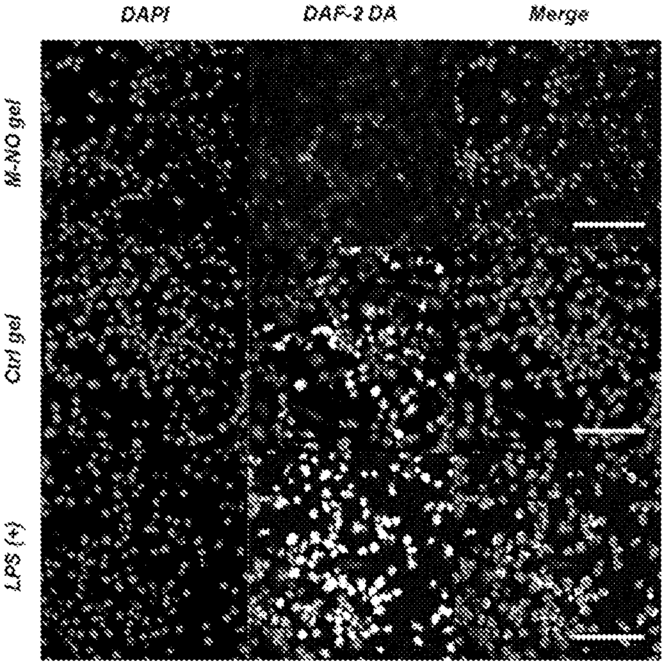
FIG. 16D shows confocal microscopy images of LPS-activated RAW 264.7 cell line after M-NO gel and control group gel treatment; intracellular NO and nuclei were stained with DAF-2 DA (green) and DAPI (blue), respectively, and the scale bar is 100 μm.

Then, washed with DPBS, treated with 10% neutral formalin (NBF) in dark conditions at room temperature, and observed through a confocal microscope after 30 minutes, and the results are shown in FIG. 16D.

As shown in FIG. 16D, high fluorescence intensity was observed in the LPS-stimulated RAW 264.7 cell line, but the signal was significantly reduced after M-NO gel treatment, confirming that the M-NO of the present disclosure can efficiently scavenge NO.

(3) Quantification of Cytokine Levels

NO is an important pro-inflammatory mediator, but its overproduction increases the levels of representative cytokines such as TNF-α and IL-6 at in vitro levels. Therefore, it was determined whether the M-NO gel of the present disclosure could reduce the levels of the cytokines TNF-α and IL-6.

Figures 17A, 17B, 17C, 17D, 17E:
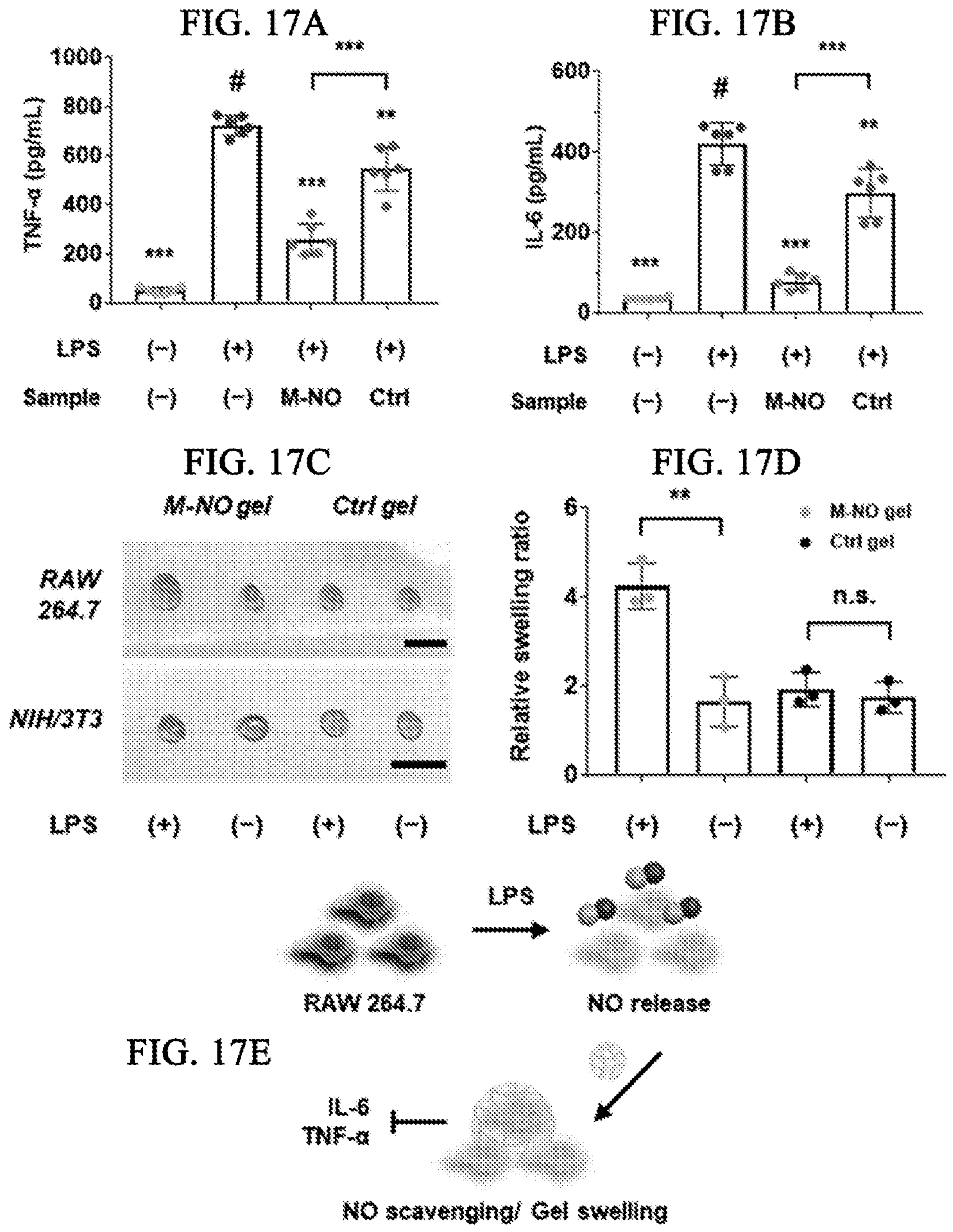
FIG. 17A shows the quantification of TNF-α levels after treatment with M-NO gel and control group gel.
FIG. 17B shows the quantification of IL-6 levels after treatment with M-NO gels and control group gels.
FIG. 17C shows images of M-NO gels and control group gels after treatment of incubated RAW 264.7 or NIH/3T3 cell lines (stimulated or not stimulated with LPS) with M-NO gels and control group gels and incubation overnight.
FIG. 17D shows the relative percentage of swelling after treating incubated RAW 264.7 or NIH/3T3 cell lines (stimulated or unstimulated with LPS) with M-NO gels and control group gels and incubating overnight.
FIG. 17E is a schematic diagram showing the in vitro NO-reactivity and scavenging ability of M-NO gels to reduce pro-inflammatory cytokine levels.

Specifically, RAW 264.7 cell lines stimulated with LPS were treated with M-NO gels and control group gels (250 μg/mL) and incubated for 24 hours, after which the pro-inflammatory cytokines TNF-α and IL-6 in the supernatant of the cell medium were quantified by ELISA, and the results are shown in FIGS. 17A and 17B.

As shown in FIGS. 17A and 17B, the levels of pro-inflammatory cytokines TNF-α and IL-6 induced by NO were significantly reduced after the M-NO gel treatment, confirming that the M-NO gel of the present disclosure can effectively scavenge the overproduced NO, thereby reducing inflammation and thus treating various inflammatory diseases.

(4) Confirmation of Swelling of M-NO Gel According to NO Capture

M-NO gels and control group gels were applied to cultured RAW 264.7 or NIH/3T3 cell lines stimulated or not stimulated by LPS and incubated overnight after treatment and checked for swelling of M-NO gels due to NO capture, the results are shown in FIGS. 17C and 17D.

As can be seen in FIGS. 17C and 17D, the M-NO gels can significantly swell in response to NO in the LPS-stimulated RAW 264.7 cell line, confirming that the M-NO gels of the present disclosure have favorable conditions for on-demand release.

Experimental Example 6 Confirmation of Treatment Effect of Rheumatoid Arthritis (1)

Figure 18A:
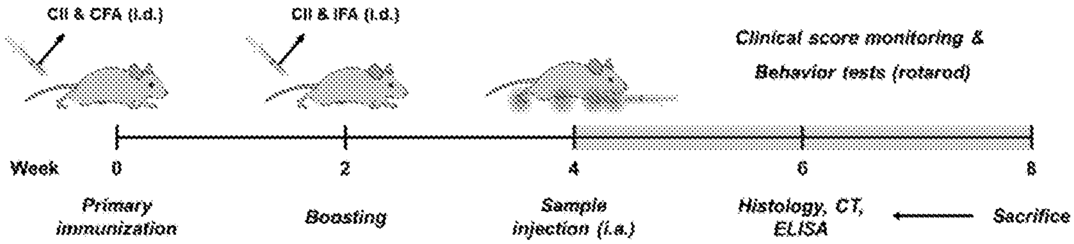
FIG. 18A shows the entire experimental timeline.

The therapeutic effect of the M-NO gel of the present disclosure on rheumatoid arthritis was confirmed in collagen-induced arthritis (CIA) mice, an animal model of rheumatoid arthritis (RA) (FIG. 18A).

(1) Preparation of Collagen-Induced Arthritis Mouse Model

Primary immunization was performed by subcutaneous injection of 100 μL of an emulsified solution (1:1, v/v) of a mixture of collagen type II (CII, 2 mg/mL) and complete Freund's adjuvant (CFA, 1 mg/mL) dissolved in 10 mM of acetic acid into the tail of 6-week-old DBA/1j mice.

Two weeks later, 100 μL of an emulsified solution (1:1, v/v) of a mixture of CII (2 mg/mL) and incomplete Freund's adjuvant (IFA, 1 mg/mL) dissolved in 10 mM of acetic acid was injected subcutaneously into the tail of the mice. 4 weeks after the first immunization, the RA model mice were randomly distributed into 8 groups, and 20 μL of each sample was injected into the joints of the CIA mice. The in-situ hybridization hydrogel was injected via a double syringe system (one syringe containing HA-N3 (2.5% by weight) and crosslinking agent (0.04% by weight), and the other syringe containing mycelium (2% by weight) and Cu(I) (0.02% by weight). Dexamethasone-carried M-NO gel was diluted 2 times to match the hydrogel system at 1% by weight (carrying amount: 5.02%, capacity: 0.5 mg/kg).

Each experimental group is classified as follows.

(A) Non-immunized healthy mice
(B) RA model mouse group treated with saline
(C) RA model mouse group treated with dexamethasone-carried micelle structure
(D) RA model mouse group treated with DA-NOCCL
(E) RA model mouse group treated with M-NO gel
(F) RA model mouse group treated with control group gel (NO non-reactive) group
(G) RA model mouse group treated with M-NO gel loaded with dexamethasone
(H) RA model mouse group treated with dexamethasone-carried control group gel (NO non-reactive)

Figure 18B:
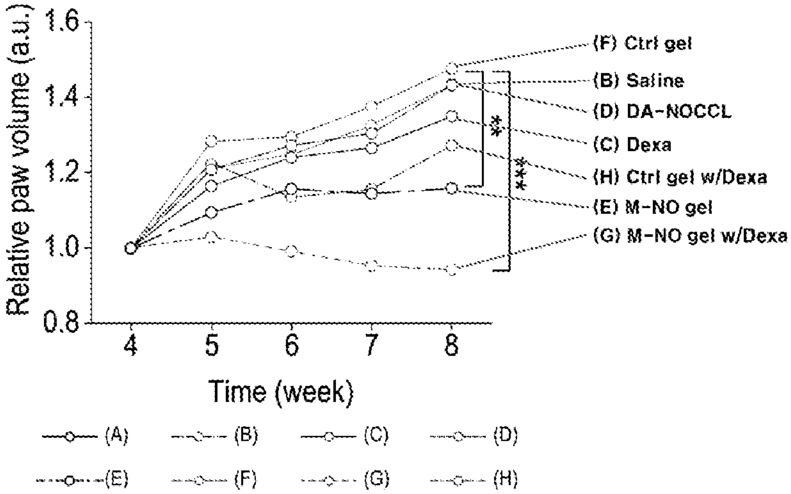
FIG. 18B shows the change in relative paw volume in the RA mouse model after sample treatment; relative paw volume was compared between the saline-treated group (B) of RA model mice to the other experimental groups and statistically analyzed using one-way ANOVA ($p<0.01$, *$p<0.001$)

(2) Confirmation of Changes in Paw Volume and Assessment Clinical Scores for Arthritis Paw volume changes over time in the RA mouse model were statistically analyzed relative to the saline-treated group (B) in each of the RA mouse model experimental groups, and the results are shown in FIG. 18B. In addition, representative mouse hind paw images at 4, 6, and 8 weeks are shown in FIG. 19.

Figure 19:
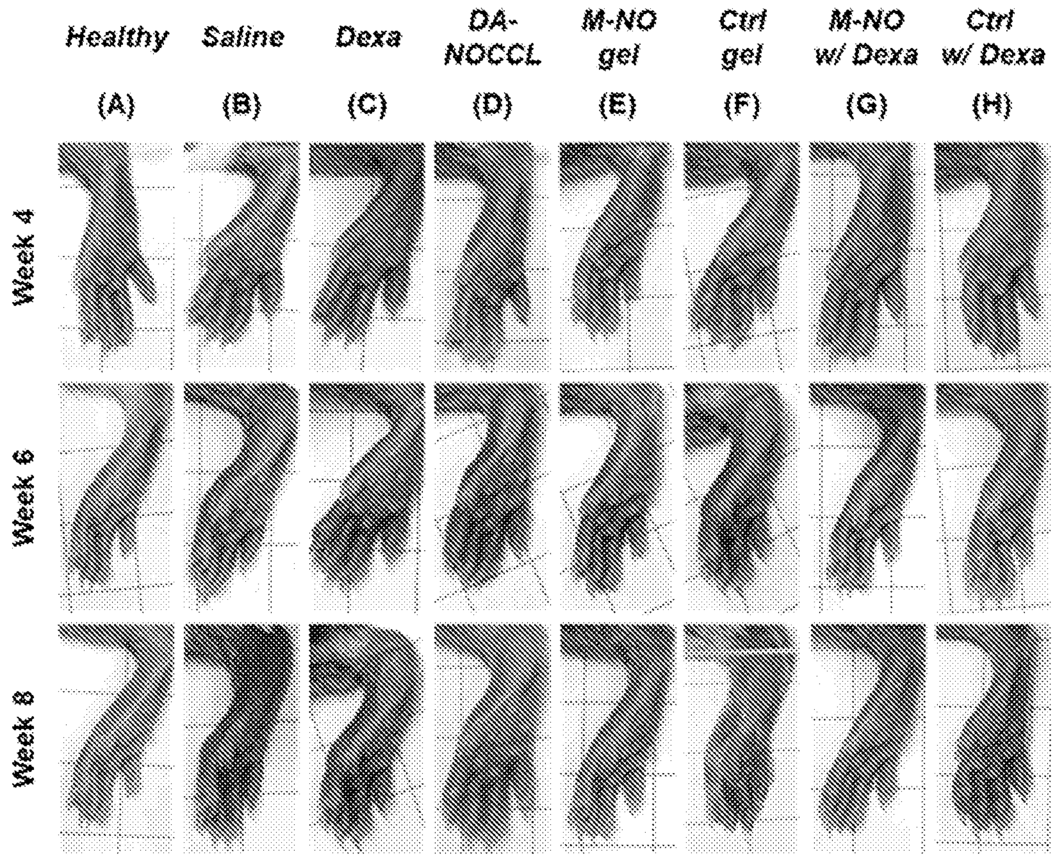

As can be seen in FIGS. 18B and 19, the groups treated with the M-NO gel of the present disclosure and the dexamethasone-carried M-NO gel exhibited significant paw volume reduction.

Figures 20A, 20B, 20C, 20D:
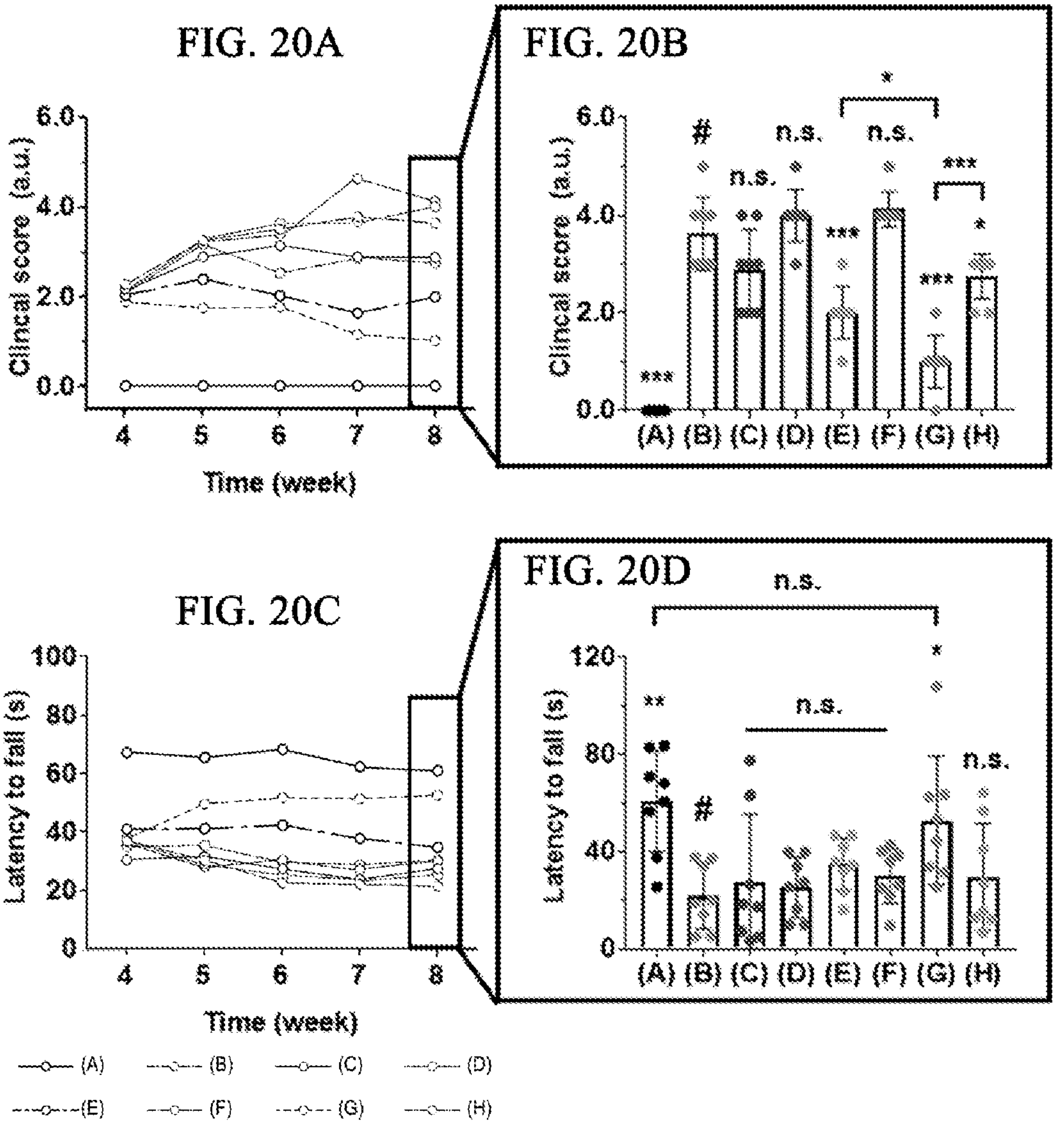
FIG. 20A shows the time-dependent mean clinical scores of RA mice after sample treatment; data are expressed as mean±SD (n=8)
FIG. 20B shows the average clinical score of RA mice at week 8 after sample treatment; RA model mice treated with saline (B) were compared to other experimental groups and statistically analyzed using one-way ANOVA ($p<0.01$, *$p<0.001$)
FIG. 20C shows the fall delay time as a function of time for RA mice after sample treatment via rotarod analysis; Data are expressed as mean±SEM (n=8)
FIG. 20D shows the fall delay time of RA mice at week 8 after sample treatment; RA model mice treated with saline (B) were compared to other experimental groups and statistically analyzed using one-way ANOVA ($p<0.01$, *$p<0.001$)

In addition, arthritis clinical scores over time were evaluated by blind testing according to standard scoring methods (scale 0-5) while monitoring clinical scores for 4 to 8 weeks, the results of which are shown in FIGS. 20A and 20B. The clinical scoring and evaluation criteria for the arthritis assessment are as follows.

0: No clinical signs
1: Minimal diffuse erythema/edema (affecting 1 or 2 toes)
2: Mild diffuse erythema/edema (affecting 3 or more toes)
3: Moderate diffuse erythema/edema (whole foot)
4: Marked diffuse erythema/edema (whole foot and ankle)
5: Severe diffuse erythema/edema (whole foot), inability to bend toes (arthrosis)

As shown in FIGS. 20A and 20B, the groups treated with the M-NO gel of the present disclosure and the dexamethasone-carried M-NO gel showed a significant reduction in clinical scores.

According to the above results, it can be confirmed that the M-NO gel and dexamethasone-carried M-NO gel of the present disclosure can not only slow down the progression of the disease but can also alleviate the symptoms of arthritis itself. In particular, the M-NO gel carried with dexamethasone showed almost complete alleviation of arthritis symptoms.

(3) Motility Assessment

Rotarod assay was performed to evaluate locomotor activity in the RA mouse model.

Specifically, before the first immunization, the mice were trained for 3 days to stay on the rotarod to reach a stable latency to fall. Thereafter, the fall delay time was recorded at a fixed speed of 10 rpm and 120 s, and the results are shown in FIGS. 20C and 20D.

As can be seen in FIGS. 20C and 20D, the groups treated with the M-NO gel of the present disclosure and the dexamethasone-carried M-NO gel exhibited increased fall latency, and in particular, the group treated with the dexamethasone-carried M-NO gel exhibited a significant increase in fall latency, indicating a progressive improvement in the motility of the mice.

Experimental Example 7 Confirmation of Treatment Effect of Rheumatoid Arthritis (2)

A series of additional experiments were conducted at week 8 to further investigate the effectiveness of the M-NO gel of the present disclosure in treating rheumatoid arthritis.

(1) Confirmation of Bone and Joint Morphology

Figure 21A:
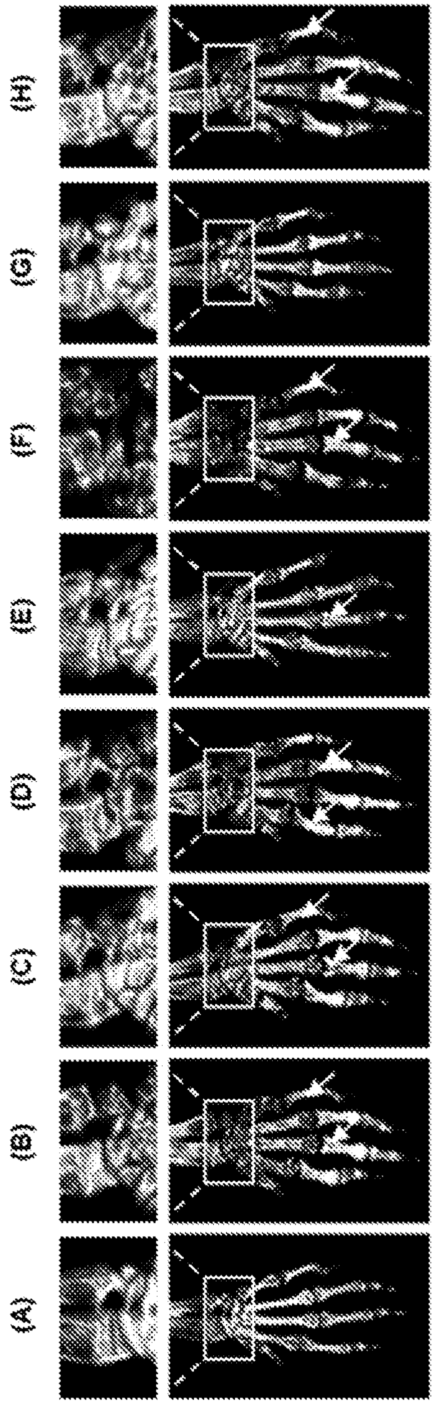
FIG. 21A shows a microcomputed tomography (micro-CT) image of the forepaw of an RA mouse model; Red arrows indicate bone destruction and damage.

The bone and joint morphology were determined by microcomputed tomography (micro-CT) images of a representative forepaw of each experimental group treated with the sample, and the results are shown in FIG. 21A.

As can be seen in FIG. 21A, compared to the other experimental groups, the group treated with the M-NO gel of the present disclosure and the dexamethasone-carried M-NO gel showed less bone erosion, allowing for a clear demarcation of the bone.

This indicates that the hydrogel of the present disclosure can prevent oxidative/nitrosative stress and upregulation of osteoclasts due to the scavenging of nitric oxide overproduced in RA lesions.

(2) Histological Assay

Figure 21B:
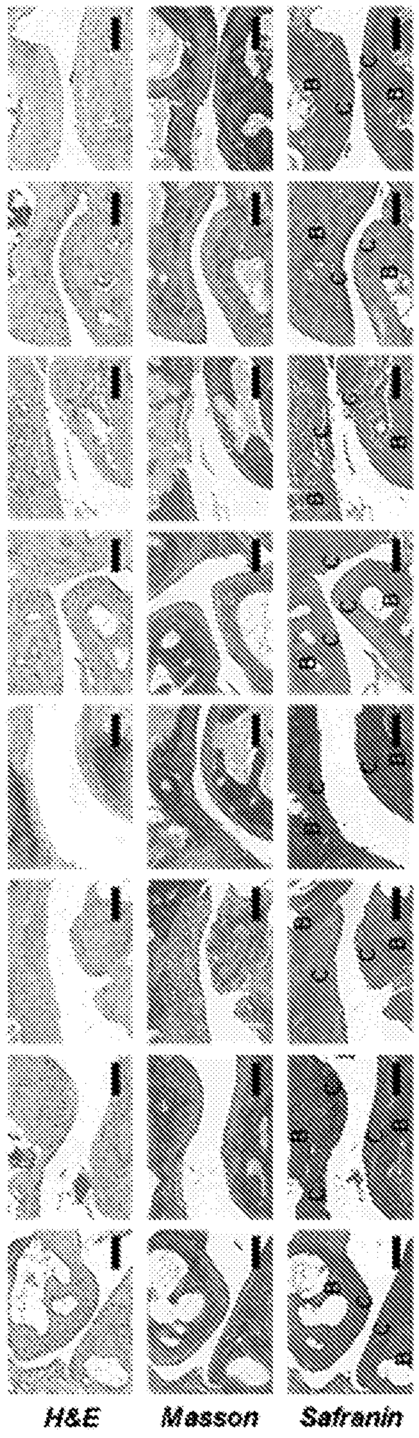
FIG. 21B shows the results of histological analysis of joint tissue after sample treatment; scale bar is 100 μm.
Figures 22A, 22B, 22C, 22D, 22E, 22F:
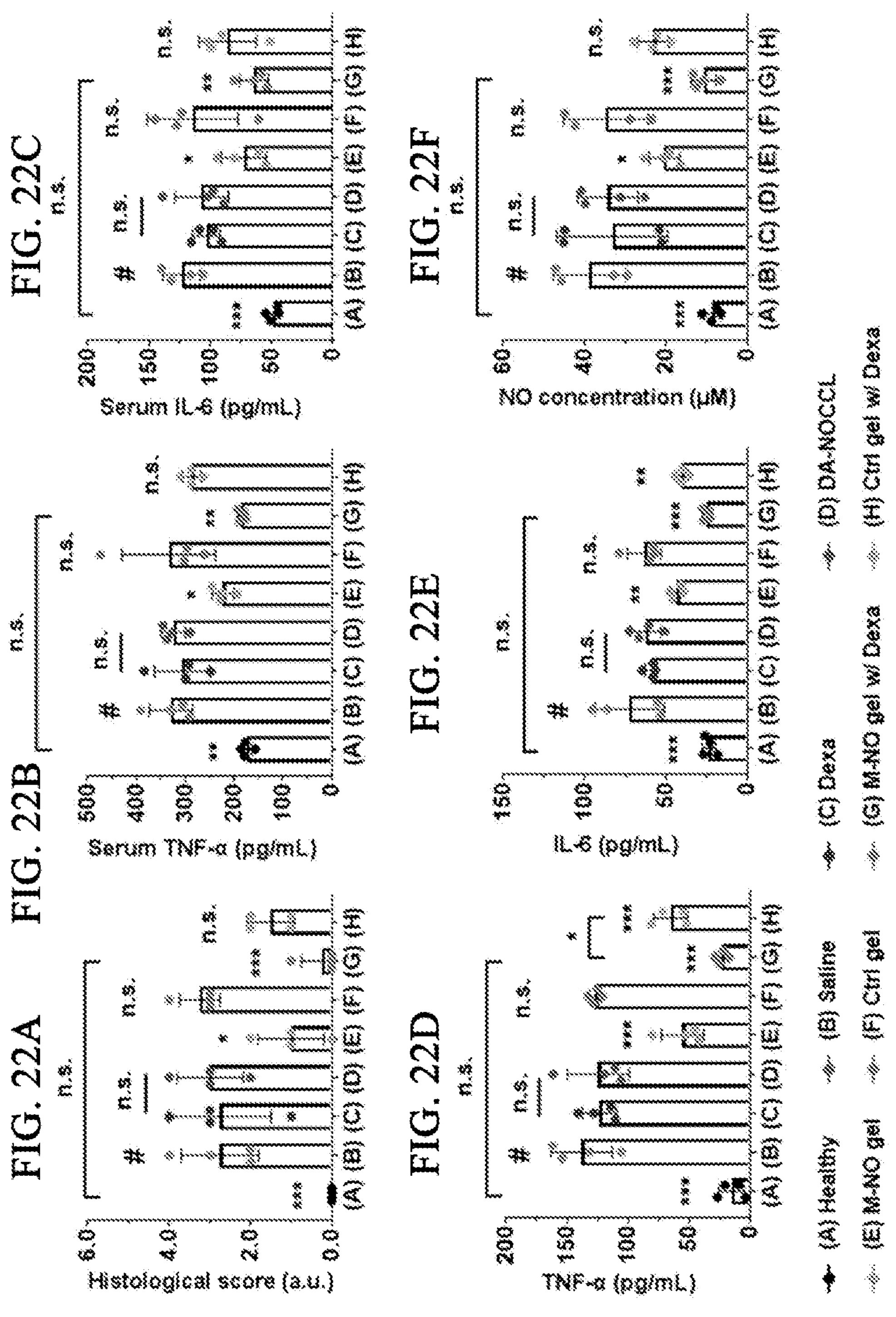
FIG. 22A shows the average histologic scores of the joint tissues determined using H&E, Masson's trichrome, and Safranin-O staining; RA model mice treated with saline (B) were compared to the other experimental groups and statistically analyzed using one-way ANOVA (*$p<0.05$, ***$p<0.001$; n.s. no significant difference)
FIG. 22B shows quantified levels of TNF-α in a sampled RA mouse serum sample.
FIG. 22C shows IL-6 in a sampled RA mouse serum specimen; Data are presented as mean±SD (n=4) and were statistically analyzed using a one-way ANOVA test with # compared to the other groups (*p<0.05, ***p<0.001; n.s. no significant difference).
FIG. 22D shows quantification of TNF-α levels in tissue fluid from sampled RA mouse paws.
FIG. 22E shows the quantification of IL-6 levels in the tissue fluid of a sampled RA mouse paws; Data are presented as mean±SD (n=4), RA model mice treated with saline (B) were compared with other experimental groups and statistically analyzed using one-way ANOVA (*p<0.05, *p<0.001; n.s. no significant difference)

The histological assays of the joint tissues of each experimental group treated with the samples were observed by staining the joint tissues of mice sacrificed at week 8 with hematoxylin and eosin (H&E), Masson's trichrome, and safranin-O. The results of the assays and the degree of cartilage damage assessed according to a standard scoring method (scale 0-4) by blind testing are shown in FIGS. 21B and 22A (B: Bone, C: Cartilage). Clinical scores and evaluation criteria are as follows.

0: No damage, normal activity

1: Minimal erosion limited to a single point

2: Mild/moderate erosion in limited scope

3: Marked/extensive erosion

4: Mostly damaged

As can be seen in FIGS. 21B and 22A above, it has been confirmed that the M-NO gel of the present disclosure and the dexamethasone-carried M-NO gel can repair the damaged cartilage and joint cavity.

(3) Confirmation of TNF-α and IL-6 Levels and NO Concentration

The levels of pro-inflammatory cytokines TNF-a and IL-6 in serum and paw tissue fluid were quantified by ELISA according to the manufacturer's protocol at week 8. NO levels were determined through grease analysis, and the results are shown in FIGS. 22B to 22E.

As shown in FIGS. 22B to 22E, pro-inflammatory cytokine levels were significantly reduced in both serum and paw tissue fluid in the groups treated with the M-NO gel of the present disclosure and the dexamethasone-carried M-NO gel. In particular, it was confirmed that the group treated with the dexamethasone-carried M-NO gel significantly decreased to a steady state.

In addition, the data quantifying the NO level in the paw tissue of the sample-treated RA mice at 8 weeks are shown in FIG. 22F. As shown in FIG. 22F, treatment with the M-NO gel of the present disclosure and the dexamethasone-carried M-NO gel significantly reduced the concentration of NO in the paw tissue fluid.

The invention claimed is:

1. An in-situ hybridization hydrogel prepared from compounds represented by the following Formulae 1 to 3:

[Formula 1]

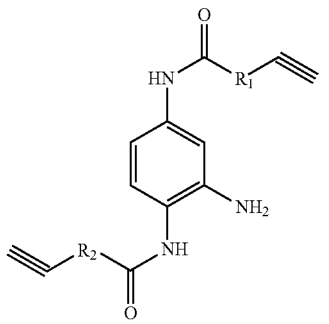

[Formula 2]

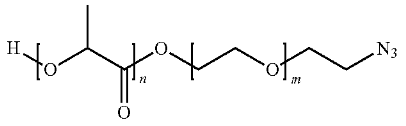

[Formula 3]

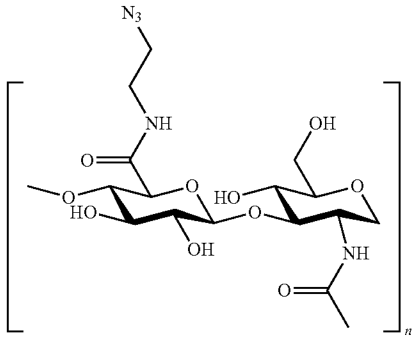

Where, $R_1$ and $R_2$ are each independently C1 to C10 alkylene, n and m are each an integer of 1 to 1000.

2. The in-situ hydrogel of claim 1, wherein $R_1$ and $R_2$ are C2 alkylene.

3. The in-situ hydrogel of claim 1, wherein the hydrogel is prepared by a click chemistry reaction between the compound represented by Formula 1 and the compounds represented by Formulae 2 and 3 above.

4. The in-situ hydrogel of claim 1, wherein the hydrogel further comprises a hydrophobic drug.

5. The in-situ hydrogel of claim 4, wherein the hydrophobic drug is carried in the micelle structure formed by self-assembly of the compound represented by Formula 2.

6. The in-situ hydrogel of claim 4, wherein the hydrophobic drug is an anti-inflammatory agent.

7. The in-situ hydrogel of claim 6, wherein the anti-inflammatory agent is dexamethasone.

8. The in-situ hydrogel of claim 4, wherein the hydrophobic drug is contained in an amount of 3% to 7% by weight relative to the total weight of the micelle structure.

9. The in-situ hydrogel of claim 1, wherein the hydrogel further comprises a hydrophobic drug and a hydrophilic drug.

* * * * *